(12) United States Patent
Appledorn et al.

(10) Patent No.: US 12,158,470 B2
(45) Date of Patent: Dec. 3, 2024

(54) METHODS AND COMPOSITIONS FOR LIVE CELL ANALYSIS OF INTRACELLULAR ATP

(71) Applicant: Sartorius BioAnalytical Instruments, Inc., Bohemia, NY (US)

(72) Inventors: Daniel Appledorn, Ann Arbor, MI (US); Cicely Schramm, Ann Arbor, MI (US); Grigory Filonov, Ann Arbor, MI (US); Kirk Schroeder, Ann Arbor, MI (US)

(73) Assignee: SARTORIUS BIOANALYTICAL INSTRUMENTS, INC., Bohemia, NY (US)

( * ) Notice: Subject to any disclaimer, the term of this patent is extended or adjusted under 35 U.S.C. 154(b) by 858 days.

(21) Appl. No.: 16/765,908

(22) PCT Filed: Mar. 7, 2019

(86) PCT No.: PCT/US2019/021171
§ 371 (c)(1),
(2) Date: May 21, 2020

(87) PCT Pub. No.: WO2019/173604
PCT Pub. Date: Sep. 12, 2019

(65) Prior Publication Data
US 2020/0400670 A1 Dec. 24, 2020

Related U.S. Application Data

(60) Provisional application No. 62/640,983, filed on Mar. 9, 2018.

(51) Int. Cl.
*C12N 15/62* (2006.01)
*C07K 1/08* (2006.01)
*G01N 21/64* (2006.01)
*G01N 33/542* (2006.01)
*G01N 33/573* (2006.01)
*G01N 33/58* (2006.01)

(52) U.S. Cl.
CPC .......... *G01N 33/5735* (2013.01); *C07K 1/082* (2013.01); *G01N 33/542* (2013.01); *G01N 33/582* (2013.01); *C07K 2319/60* (2013.01); *C12Q 2563/107* (2013.01)

(58) Field of Classification Search
None
See application file for complete search history.

(56) References Cited

FOREIGN PATENT DOCUMENTS

| EP | 2 141 230 | 3/2008 |
|---|---|---|
| WO | 2005/036178 | 4/2005 |
| WO | 2015/108102 | 7/2015 |
| WO | 2017/094885 | 6/2017 |

OTHER PUBLICATIONS

Ko et al., "Genetically encoded FRET sensors using a fluorescent unnatural amino acid as a FRET donor", RSC Adv. 6:78661-78668, 2016 (Year: 2016).*
Xia et al., "Reliable and Global Measurement of Fluorescence Resonance Energy Transfer Using Fluorescence Microscopes", Biophys. J. 81:2395-2402, 2001 (Year: 2001).*
Chen et al., "Fusion protein linkers: Property, design and functionality," Advanced Drug Delivery Reviews 65:1357-1369, 2013 (Year: 2013).*
The International Search Report (ISR) with Written Opinion for PCT/US2019/021171 dated May 28, 2019, pp. 1-17.
Nakano, Masahiro et al. "Ca 2+ Regulation of Mitochondrial ATP Synthesis Visualized at the Single Cell Level" ACS Chemical Biology (2011) vol. 6(7), pp. 709-715.
Su, Ting et al. "Monitoring of dual bio-molecular events using FRET biosensors based on mTagBFP/sfGFP and mVenus/mKOK fluorescent protein pairs" Biosensors and Bioelectronics (2013) vol. 46, pp. 97-101.
Schramm, et al., "Direct measurements of cellular ATP levels in tumor cell lines using real-time, quantitative live-cell analysis," American Academy Cancer Research meeting, abstract (Apr. 15, 2018).
Schramm,et al., "Direct measurements of cellular ATP levels using automated, quantitative live-cell analysis for mitochondrial toxicity screening," Society of Toxicology meeting, abstract (Mar. 10, 2018).
Kaur, et al., "A linker strategy for Trans-FRET assay to determine activation intermediate of NEDDylation cascade," Biotechnology and Bioengineering, 2014, vol. 111, No. 7,pp. 1288-1295.

* cited by examiner

*Primary Examiner* — David Steadman
(74) *Attorney, Agent, or Firm* — MCDONNELL BOEHNEN HULBERT & BERGHOFF LLP

(57) ABSTRACT

Disclosed herein are ATP biosensor fusion proteins and their use for assaying ATP levels in cells.

22 Claims, 9 Drawing Sheets
Specification includes a Sequence Listing.

SEQUENCE LISTING

```
<160> NUMBER OF SEQ ID NOS: 22

<210> SEQ ID NO 1
<211> LENGTH: 218
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: optionally absent
<220> FEATURE:
<221> NAME/KEY: MISC_FEATURE
<222> LOCATION: (217)..(218)
<223> OTHER INFORMATION: optionally absent

<400> SEQUENCE: 1

Met Val Ser Val Ile Lys Pro Glu Met Lys Met Arg Tyr Tyr Met Asp
1               5                   10                  15
```

```
Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
 50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
                180                 185                 190

His Tyr Ile Gly His Arg Leu Val Arg Lys Thr Glu Gly Asn Ile Thr
            195                 200                 205

Glu Gln Val Glu Asp Ala Val Ala His Ser
        210                 215

<210> SEQ ID NO 2
<211> LENGTH: 217
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: optionally absent
<220> FEATURE:
<221> NAME/KEY: MISC_FEATURE
<222> LOCATION: (216)..(217)
<223> OTHER INFORMATION: optionally absent

<400> SEQUENCE: 2

Met Ser Val Ile Lys Pro Glu Met Lys Met Arg Tyr Tyr Met Asp Gly
1               5                   10                  15

Ser Val Asn Gly His Glu Phe Thr Ile Glu Gly Glu Gly Thr Gly Arg
            20                  25                  30

Pro Tyr Glu Gly His Gln Glu Met Thr Leu Arg Val Thr Met Ala Lys
        35                  40                  45

Gly Gly Pro Met Pro Phe Ala Phe Asp Leu Val Ser His Val Phe Cys
 50                  55                  60

Tyr Gly His Arg Pro Phe Thr Lys Tyr Pro Glu Glu Ile Pro Asp Tyr
65                  70                  75                  80

Phe Lys Gln Ala Phe Pro Glu Gly Leu Ser Trp Glu Arg Ser Leu Glu
                85                  90                  95

Phe Glu Asp Gly Gly Ser Ala Ser Val Ser Ala His Ile Ser Leu Arg
            100                 105                 110

Gly Asn Thr Phe Tyr His Lys Ser Lys Phe Thr Gly Val Asn Phe Pro
```

```
            115                 120                 125

Ala Asp Gly Pro Ile Met Gln Asn Gln Ser Val Asp Trp Glu Pro Ser
        130                 135                 140

Thr Glu Lys Ile Thr Ala Ser Asp Gly Val Leu Lys Gly Asp Val Thr
145                 150                 155                 160

Met Tyr Leu Lys Leu Glu Gly Gly Gly Asn His Lys Cys Gln Phe Lys
                165                 170                 175

Thr Thr Tyr Lys Ala Ala Lys Lys Ile Leu Lys Met Pro Gly Ser His
            180                 185                 190

Tyr Ile Ser His Arg Leu Val Arg Lys Thr Glu Gly Asn Ile Thr Glu
        195                 200                 205

Leu Val Glu Asp Ala Val Ala His Ser
    210                 215

<210> SEQ ID NO 3
<211> LENGTH: 218
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: optionally absent
<220> FEATURE:
<221> NAME/KEY: MISC_FEATURE
<222> LOCATION: (217)..(218)
<223> OTHER INFORMATION: optionally absent

<400> SEQUENCE: 3

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Met
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser
    210                 215
```

<210> SEQ ID NO 4
<211> LENGTH: 246
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: optionally absent
<220> FEATURE:
<221> NAME/KEY: MISC_FEATURE
<222> LOCATION: (34)..(34)
<223> OTHER INFORMATION: Xaa is A or K
<220> FEATURE:
<221> NAME/KEY: MISC_FEATURE
<222> LOCATION: (245)..(246)
<223> OTHER INFORMATION: optionally absent

<400> SEQUENCE: 4

Asp Gly Ser Val Gln Leu Ala Asp His Tyr Gln Gln Asn Thr Pro Ile
1               5                   10                  15

Gly Asp Gly Pro Val Leu Leu Pro Asp Asn His Tyr Leu Ser Thr Gln
            20                  25                  30

Ser Xaa Leu Ser Lys Asp Pro Asn Glu Lys Arg Asp His Met Val Leu
        35                  40                  45

Leu Glu Phe Val Thr Ala Ala Gly Ile Thr Leu Gly Met Asp Glu Leu
50                  55                  60

Tyr Lys Gly Gly Ser Gly Gly Met Val Ser Lys Gly Glu Glu Leu Phe
65                  70                  75                  80

Thr Gly Val Val Pro Ile Leu Val Glu Leu Asp Gly Asp Val Asn Gly
                85                  90                  95

His Lys Phe Ser Val Ser Gly Glu Gly Glu Gly Asp Ala Thr Tyr Gly
            100                 105                 110

Lys Leu Thr Leu Lys Phe Ile Cys Thr Thr Gly Lys Leu Pro Val Pro
        115                 120                 125

Trp Pro Thr Leu Val Thr Thr Leu Thr Tyr Gly Val Gln Cys Phe Ser
130                 135                 140

Arg Tyr Pro Asp His Met Lys Gln His Asp Phe Phe Lys Ser Ala Met
145                 150                 155                 160

Pro Glu Gly Tyr Val Gln Glu Arg Thr Ile Phe Phe Lys Asp Asp Gly
                165                 170                 175

Asn Tyr Lys Thr Arg Ala Glu Val Lys Phe Glu Gly Asp Thr Leu Val
            180                 185                 190

Asn Arg Ile Glu Leu Lys Gly Ile Asp Phe Lys Glu Asp Gly Asn Ile
        195                 200                 205

Leu Gly His Lys Leu Glu Tyr Asn Tyr Asn Ser His Asn Val Tyr Ile
210                 215                 220

Met Ala Asp Lys Gln Lys Asn Gly Ile Lys Val Asn Phe Lys Ile Arg
225                 230                 235                 240

His Asn Ile Glu Glu Ala
                245

<210> SEQ ID NO 5
<211> LENGTH: 132
<212> TYPE: PRT
<213> ORGANISM: Artificial Sequence
<220> FEATURE:
<223> OTHER INFORMATION: Synthetic
<220> FEATURE:

<221> NAME/KEY: MISC_FEATURE
<222> LOCATION: (1)..(1)
<223> OTHER INFORMATION: optionally absent

<400> SEQUENCE: 5

Met Lys Thr Val Lys Val Asn Ile Thr Thr Pro Asp Gly Pro Val Tyr
1               5                   10                  15

Asp Ala Asp Ile Glu Met Val Ser Val Arg Ala Glu Ser Gly Asp Leu
            20                  25                  30

Gly Ile Leu Pro Gly His Ile Pro Thr Lys Ala Pro Leu Lys Ile Gly
        35                  40                  45

Ala Val Arg Leu Lys Lys Asp Gly Gln Thr Glu Met Val Ala Val Ser
    50                  55                  60

Gly Gly Thr Val Glu Val Arg Pro Asp His Val Thr Ile Asn Ala Gln
65                  70                  75                  80

Ala Ala Glu Thr Ala Glu Gly Ile Asp Lys Glu Arg Ala Glu Ala Ala
                85                  90                  95

Arg Gln Arg Ala Gln Glu Arg Leu Asn Ser Gln Ser Asp Asp Thr Asp
            100                 105                 110

Ile Arg Arg Ala Glu Leu Ala Leu Gln Arg Ala Leu Asn Arg Leu Asp
        115                 120                 125

Val Ala Gly Lys
    130

<210> SEQ ID NO 6
<211> LENGTH: 133
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 6

Met Lys Thr Val Lys Val Asn Ile Thr Thr Pro Asp Gly Pro Val Tyr
1               5                   10                  15

Asp Ala Asp Ile Glu Met Val Ser Val Arg Ala Glu Ser Gly Asp Leu
            20                  25                  30

Gly Ile Leu Pro Gly His Ile Pro Thr Lys Ala Pro Leu Lys Ile Gly
        35                  40                  45

Ala Val Arg Leu Lys Lys Asp Gly Gln Thr Glu Tyr Val Ala Val Ser
    50                  55                  60

Gly Gly Thr Val Glu Val Arg Pro Asp His Val Thr Ile Asn Ala Gln
65                  70                  75                  80

Ala Ala Glu Thr Ala Glu Gly Ile Asp Lys Glu Arg Ala Glu Ala Ala
                85                  90                  95

Arg Gln Arg Ala Gln Glu Arg Leu Asn Ser Gln Ser Asp Asp Thr Asp
            100                 105                 110

Ile Arg Arg Ala Glu Leu Ala Leu Gln Arg Ala Leu Asn Arg Leu Asp
        115                 120                 125

Val Ala Glu Met Lys
    130

<210> SEQ ID NO 7
<211> LENGTH: 598
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (220)..(220)
<223> OTHER INFORMATION: optionally absent

<400> SEQUENCE: 7
```

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Ala Met Lys Thr Val Lys
    210                 215                 220

Val Asn Ile Thr Thr Pro Asp Gly Pro Val Tyr Asp Ala Asp Ile Glu
225                 230                 235                 240

Met Val Ser Val Arg Ala Glu Ser Gly Asp Leu Gly Ile Leu Pro Gly
                245                 250                 255

His Ile Pro Thr Lys Ala Pro Leu Lys Ile Gly Ala Val Arg Leu Lys
            260                 265                 270

Lys Asp Gly Gln Thr Glu Met Val Ala Val Ser Gly Gly Thr Val Glu
        275                 280                 285

Val Arg Pro Asp His Val Thr Ile Asn Ala Gln Ala Ala Glu Thr Ala
    290                 295                 300

Glu Gly Ile Asp Lys Glu Arg Ala Glu Ala Arg Gln Arg Ala Gln
305                 310                 315                 320

Glu Arg Leu Asn Ser Gln Ser Asp Asp Thr Asp Ile Arg Arg Ala Glu
                325                 330                 335

Leu Ala Leu Gln Arg Ala Leu Asn Arg Leu Asp Val Ala Gly Lys Ala
            340                 345                 350

```
Asp Gly Ser Val Gln Leu Ala Asp His Tyr Gln Asn Thr Pro Ile
        355                 360                 365

Gly Asp Gly Pro Val Leu Leu Pro Asp Asn His Tyr Leu Ser Thr Gln
370                 375                 380

Ser Lys Leu Ser Lys Asp Pro Asn Glu Lys Arg Asp His Met Val Leu
385                 390                 395                 400

Leu Glu Phe Val Thr Ala Ala Gly Ile Thr Leu Gly Met Asp Glu Leu
                405                 410                 415

Tyr Lys Gly Gly Ser Gly Gly Met Val Ser Lys Gly Glu Glu Leu Phe
            420                 425                 430

Thr Gly Val Val Pro Ile Leu Val Glu Leu Asp Gly Asp Val Asn Gly
        435                 440                 445

His Lys Phe Ser Val Ser Gly Glu Gly Glu Gly Asp Ala Thr Tyr Gly
    450                 455                 460

Lys Leu Thr Leu Lys Phe Ile Cys Thr Thr Gly Lys Leu Pro Val Pro
465                 470                 475                 480

Trp Pro Thr Leu Val Thr Thr Leu Thr Tyr Gly Val Gln Cys Phe Ser
                485                 490                 495

Arg Tyr Pro Asp His Met Lys Gln His Asp Phe Phe Lys Ser Ala Met
            500                 505                 510

Pro Glu Gly Tyr Val Gln Glu Arg Thr Ile Phe Phe Lys Asp Asp Gly
        515                 520                 525

Asn Tyr Lys Thr Arg Ala Glu Val Lys Phe Glu Gly Asp Thr Leu Val
    530                 535                 540

Asn Arg Ile Glu Leu Lys Gly Ile Asp Phe Lys Glu Asp Gly Asn Ile
545                 550                 555                 560

Leu Gly His Lys Leu Glu Tyr Asn Tyr Asn Ser His Asn Val Tyr Ile
                565                 570                 575

Met Ala Asp Lys Gln Lys Asn Gly Ile Lys Val Asn Phe Lys Ile Arg
            580                 585                 590

His Asn Ile Glu Glu Ala
        595

<210> SEQ ID NO 8
<211> LENGTH: 598
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (220)..(220)
<223> OTHER INFORMATION: optionally absent

<400> SEQUENCE: 8

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
```

```
                65                  70                  75                  80
        Tyr Phe Lys Gln Ala Phe Pro Glu Gly Leu Ser Trp Glu Arg Ser Leu
                            85                  90                  95

Glu Phe Glu Asp Gly Gly Ser Ala Ser Val Ser Ala His Ile Ser Leu
                            100                 105                 110

Arg Gly Asn Thr Phe Tyr His Lys Ser Lys Phe Thr Gly Val Asn Phe
                            115                 120                 125

Pro Ala Asp Gly Pro Ile Met Gln Asn Gln Ser Val Asp Trp Glu Pro
                            130                 135                 140

Ser Thr Glu Lys Ile Thr Ala Ser Asp Gly Val Leu Lys Gly Asp Val
        145                 150                 155                 160

Thr Met Tyr Leu Lys Leu Glu Gly Gly Asn His Lys Cys Gln Phe
                            165                 170                 175

Lys Thr Thr Tyr Lys Ala Ala Lys Glu Ile Leu Glu Met Pro Gly Asp
                            180                 185                 190

His Tyr Ile Gly His Arg Leu Val Arg Lys Thr Glu Gly Asn Ile Thr
                            195                 200                 205

Glu Gln Val Glu Asp Ala Val Ala His Ser Ser Met Lys Thr Val Lys
                            210                 215                 220

Val Asn Ile Thr Thr Pro Asp Gly Pro Val Tyr Asp Ala Asp Ile Glu
        225                 230                 235                 240

Met Val Ser Val Arg Ala Glu Ser Gly Asp Leu Gly Ile Leu Pro Gly
                            245                 250                 255

His Ile Pro Thr Lys Ala Pro Leu Lys Ile Gly Ala Val Arg Leu Lys
                            260                 265                 270

Lys Asp Gly Gln Thr Glu Met Val Ala Val Ser Gly Thr Val Glu
                            275                 280                 285

Val Arg Pro Asp His Val Thr Ile Asn Ala Gln Ala Glu Thr Ala
                            290                 295                 300

Glu Gly Ile Asp Lys Glu Arg Ala Glu Ala Arg Gln Arg Ala Gln
        305                 310                 315                 320

Glu Arg Leu Asn Ser Gln Ser Asp Asp Thr Asp Ile Arg Arg Ala Glu
                            325                 330                 335

Leu Ala Leu Gln Arg Ala Leu Asn Arg Leu Asp Val Ala Gly Lys Ala
                            340                 345                 350

Asp Gly Ser Val Gln Leu Ala Asp His Tyr Gln Gln Asn Thr Pro Ile
                            355                 360                 365

Gly Asp Gly Pro Val Leu Leu Pro Asp Asn His Tyr Leu Ser Thr Gln
                            370                 375                 380

Ser Lys Leu Ser Lys Asp Pro Asn Glu Lys Arg Asp His Met Val Leu
        385                 390                 395                 400

Leu Glu Phe Val Thr Ala Ala Gly Ile Thr Leu Gly Met Asp Glu Leu
                            405                 410                 415

Tyr Lys Gly Gly Ser Gly Gly Met Val Ser Lys Gly Glu Glu Leu Phe
                            420                 425                 430

Thr Gly Val Val Pro Ile Leu Val Glu Leu Asp Gly Asp Val Asn Gly
                            435                 440                 445

His Lys Phe Ser Val Ser Gly Glu Gly Glu Gly Asp Ala Thr Tyr Gly
                            450                 455                 460

Lys Leu Thr Leu Lys Phe Ile Cys Thr Thr Gly Lys Leu Pro Val Pro
        465                 470                 475                 480

Trp Pro Thr Leu Val Thr Thr Leu Thr Tyr Gly Val Gln Cys Phe Ser
                            485                 490                 495
```

Arg Tyr Pro Asp His Met Lys Gln His Asp Phe Phe Lys Ser Ala Met
                500                 505                 510

Pro Glu Gly Tyr Val Gln Glu Arg Thr Ile Phe Phe Lys Asp Asp Gly
            515                 520                 525

Asn Tyr Lys Thr Arg Ala Glu Val Lys Phe Glu Gly Asp Thr Leu Val
        530                 535                 540

Asn Arg Ile Glu Leu Lys Gly Ile Asp Phe Lys Glu Asp Gly Asn Ile
545                 550                 555                 560

Leu Gly His Lys Leu Glu Tyr Asn Tyr Asn Ser His Asn Val Tyr Ile
                565                 570                 575

Met Ala Asp Lys Gln Lys Asn Gly Ile Lys Val Asn Phe Lys Ile Arg
            580                 585                 590

His Asn Ile Glu Glu Ala
        595

<210> SEQ ID NO 9
<211> LENGTH: 598
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (219)..(219)
<223> OTHER INFORMATION: optionally absent

<400> SEQUENCE: 9

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Met Lys Thr Val Lys Val
210             215                 220

Asn Ile Thr Thr Pro Asp Gly Pro Val Tyr Asp Ala Asp Ile Glu Met
225             230                 235                 240

Val Ser Val Arg Ala Glu Ser Gly Asp Leu Gly Ile Leu Pro Gly His
        245                 250                 255

Ile Pro Thr Lys Ala Pro Leu Lys Ile Gly Ala Val Arg Leu Lys Lys
            260                 265                 270

Asp Gly Gln Thr Glu Met Val Ala Val Ser Gly Thr Val Glu Val
        275                 280                 285

Arg Pro Asp His Val Thr Ile Asn Ala Gln Ala Glu Thr Ala Glu
290                 295                 300

Gly Ile Asp Lys Glu Arg Ala Glu Ala Ala Arg Gln Arg Ala Gln Glu
305             310                 315                 320

Arg Leu Asn Ser Gln Ser Asp Thr Asp Ile Arg Arg Ala Glu Leu
            325                 330                 335

Ala Leu Gln Arg Ala Leu Asn Arg Leu Asp Val Ala Gly Lys Phe Phe
        340                 345                 350

Asp Gly Ser Val Gln Leu Ala Asp His Tyr Gln Gln Asn Thr Pro Ile
        355                 360                 365

Gly Asp Gly Pro Val Leu Leu Pro Asp Asn His Tyr Leu Ser Thr Gln
370                 375                 380

Ser Lys Leu Ser Lys Asp Pro Asn Glu Lys Arg Asp His Met Val Leu
385                 390                 395                 400

Leu Glu Phe Val Thr Ala Ala Gly Ile Thr Leu Gly Met Asp Glu Leu
                405                 410                 415

Tyr Lys Gly Gly Ser Gly Gly Met Val Ser Lys Gly Glu Glu Leu Phe
            420                 425                 430

Thr Gly Val Val Pro Ile Leu Val Glu Leu Asp Gly Asp Val Asn Gly
        435                 440                 445

His Lys Phe Ser Val Ser Gly Glu Gly Glu Gly Asp Ala Thr Tyr Gly
        450                 455                 460

Lys Leu Thr Leu Lys Phe Ile Cys Thr Thr Gly Lys Leu Pro Val Pro
465                 470                 475                 480

Trp Pro Thr Leu Val Thr Thr Leu Thr Tyr Gly Val Gln Cys Phe Ser
                485                 490                 495

Arg Tyr Pro Asp His Met Lys Gln His Asp Phe Phe Lys Ser Ala Met
            500                 505                 510

Pro Glu Gly Tyr Val Gln Glu Arg Thr Ile Phe Phe Lys Asp Asp Gly
        515                 520                 525

Asn Tyr Lys Thr Arg Ala Glu Val Lys Phe Glu Gly Asp Thr Leu Val
        530                 535                 540

Asn Arg Ile Glu Leu Lys Gly Ile Asp Phe Lys Glu Asp Gly Asn Ile
545                 550                 555                 560

Leu Gly His Lys Leu Glu Tyr Asn Tyr Asn Ser His Asn Val Tyr Ile
            565                 570                 575

Met Ala Asp Lys Gln Lys Asn Gly Ile Lys Val Asn Phe Lys Ile Arg
        580                 585                 590

His Asn Ile Glu Glu Ala
        595

<210> SEQ ID NO 10
<211> LENGTH: 599
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (220)..(220)
<223> OTHER INFORMATION: optionally absent

<400> SEQUENCE: 10
```

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
                20                  25                  30

Arg Pro Tyr Glu Gly His Gln Glu Met Thr Leu Arg Val Thr Met Ala
            35                  40                  45

Glu Gly Gly Pro Met Pro Phe Ala Phe Asp Leu Val Ser His Val Phe
        50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Val Met Lys Thr Val Lys
210                 215                 220

Val Asn Ile Thr Thr Pro Asp Gly Pro Val Tyr Asp Ala Asp Ile Glu
225                 230                 235                 240

Met Val Ser Val Arg Ala Glu Ser Gly Asp Leu Gly Ile Leu Pro Gly
                245                 250                 255

His Ile Pro Thr Lys Ala Pro Leu Lys Ile Gly Ala Val Arg Leu Lys
            260                 265                 270

Lys Asp Gly Gln Thr Glu Met Val Ala Val Ser Gly Gly Thr Val Glu
        275                 280                 285

Val Arg Pro Asp His Val Thr Ile Asn Ala Gln Ala Ala Glu Thr Ala
290                 295                 300

Glu Gly Ile Asp Lys Glu Arg Ala Glu Ala Arg Gln Arg Ala Gln
305                 310                 315                 320

Glu Arg Leu Asn Ser Gln Ser Asp Asp Thr Asp Ile Arg Arg Ala Glu
                325                 330                 335

Leu Ala Leu Gln Arg Ala Leu Asn Arg Leu Asp Val Ala Gly Lys Phe
            340                 345                 350

```
Leu Asp Gly Ser Val Gln Leu Ala Asp His Tyr Gln Gln Asn Thr Pro
        355                 360                 365

Ile Gly Asp Gly Pro Val Leu Leu Pro Asp Asn His Tyr Leu Ser Thr
370                 375                 380

Gln Ser Lys Leu Ser Lys Asp Pro Asn Glu Lys Arg Asp His Met Val
385                 390                 395                 400

Leu Leu Glu Phe Val Thr Ala Ala Gly Ile Thr Leu Gly Met Asp Glu
                405                 410                 415

Leu Tyr Lys Gly Gly Ser Gly Gly Met Val Ser Lys Gly Glu Glu Leu
            420                 425                 430

Phe Thr Gly Val Val Pro Ile Leu Val Glu Leu Asp Gly Asp Val Asn
        435                 440                 445

Gly His Lys Phe Ser Val Ser Gly Glu Gly Glu Gly Asp Ala Thr Tyr
    450                 455                 460

Gly Lys Leu Thr Leu Lys Phe Ile Cys Thr Thr Gly Lys Leu Pro Val
465                 470                 475                 480

Pro Trp Pro Thr Leu Val Thr Thr Leu Thr Tyr Gly Val Gln Cys Phe
                485                 490                 495

Ser Arg Tyr Pro Asp His Met Lys Gln His Asp Phe Phe Lys Ser Ala
            500                 505                 510

Met Pro Glu Gly Tyr Val Gln Glu Arg Thr Ile Phe Phe Lys Asp Asp
        515                 520                 525

Gly Asn Tyr Lys Thr Arg Ala Glu Val Lys Phe Glu Gly Asp Thr Leu
    530                 535                 540

Val Asn Arg Ile Glu Leu Lys Gly Ile Asp Phe Lys Glu Asp Gly Asn
545                 550                 555                 560

Ile Leu Gly His Lys Leu Glu Tyr Asn Tyr Asn Ser His Asn Val Tyr
                565                 570                 575

Ile Met Ala Asp Lys Gln Lys Asn Gly Ile Lys Val Asn Phe Lys Ile
            580                 585                 590

Arg His Asn Ile Glu Glu Ala
        595

<210> SEQ ID NO 11
<211> LENGTH: 601
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (220)..(220)
<223> OTHER INFORMATION: optionally absent

<400> SEQUENCE: 11

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60
```

```
Cys Tyr Gly His Arg Val Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
                180                 185                 190

His Tyr Ile Gly His Arg Leu Val Arg Lys Thr Glu Gly Asn Ile Thr
            195                 200                 205

Glu Gln Val Glu Asp Ala Val Ala His Ser Thr Met Lys Thr Val Lys
    210                 215                 220

Val Asn Ile Thr Thr Pro Asp Gly Pro Val Tyr Asp Ala Asp Ile Glu
225                 230                 235                 240

Met Val Ser Val Arg Ala Glu Ser Gly Asp Leu Gly Ile Leu Pro Gly
                245                 250                 255

His Ile Pro Thr Lys Ala Pro Leu Lys Ile Gly Ala Val Arg Leu Lys
            260                 265                 270

Lys Asp Gly Gln Thr Glu Met Val Ala Val Ser Gly Gly Thr Val Glu
        275                 280                 285

Val Arg Pro Asp His Val Thr Ile Asn Ala Gln Ala Ala Glu Thr Ala
    290                 295                 300

Glu Gly Ile Asp Lys Glu Arg Ala Glu Ala Ala Arg Gln Arg Ala Gln
305                 310                 315                 320

Glu Arg Leu Asn Ser Gln Ser Asp Asp Thr Asp Ile Arg Arg Ala Glu
                325                 330                 335

Leu Ala Leu Gln Arg Ala Leu Asn Arg Leu Asp Val Ala Gly Lys Gly
            340                 345                 350

Thr Ser Gly Asp Gly Ser Val Gln Leu Ala Asp His Tyr Gln Gln Asn
        355                 360                 365

Thr Pro Ile Gly Asp Gly Pro Val Leu Leu Pro Asp Asn His Tyr Leu
    370                 375                 380

Ser Thr Gln Ser Lys Leu Ser Lys Asp Pro Asn Glu Lys Arg Asp His
385                 390                 395                 400

Met Val Leu Leu Glu Phe Val Thr Ala Ala Gly Ile Thr Leu Gly Met
                405                 410                 415

Asp Glu Leu Tyr Lys Gly Gly Ser Gly Gly Met Val Ser Lys Gly Glu
            420                 425                 430

Glu Leu Phe Thr Gly Val Val Pro Ile Leu Val Glu Leu Asp Gly Asp
        435                 440                 445

Val Asn Gly His Lys Phe Ser Val Ser Gly Glu Gly Glu Gly Asp Ala
    450                 455                 460

Thr Tyr Gly Lys Leu Thr Leu Lys Phe Ile Cys Thr Thr Gly Lys Leu
465                 470                 475                 480

Pro Val Pro Trp Pro Thr Leu Val Thr Thr Leu Thr Tyr Gly Val Gln
```

```
                    485                 490                 495

Cys Phe Ser Arg Tyr Pro Asp His Met Lys Gln His Asp Phe Phe Lys
                500                 505                 510

Ser Ala Met Pro Glu Gly Tyr Val Gln Glu Arg Thr Ile Phe Phe Lys
                515                 520                 525

Asp Asp Gly Asn Tyr Lys Thr Arg Ala Glu Val Lys Phe Glu Gly Asp
            530                 535                 540

Thr Leu Val Asn Arg Ile Glu Leu Lys Gly Ile Asp Phe Lys Glu Asp
545                 550                 555                 560

Gly Asn Ile Leu Gly His Lys Leu Glu Tyr Asn Tyr Asn Ser His Asn
                565                 570                 575

Val Tyr Ile Met Ala Asp Lys Gln Lys Asn Gly Ile Lys Val Asn Phe
                580                 585                 590

Lys Ile Arg His Asn Ile Glu Glu Ala
                595                 600

<210> SEQ ID NO 12
<211> LENGTH: 132
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 12

Met Lys Thr Val Lys Val Asn Ile Thr Thr Pro Asp Gly Pro Val Tyr
1               5                   10                  15

Asp Ala Asp Ile Glu Met Val Ser Val Arg Ala Glu Ser Gly Asp Leu
                20                  25                  30

Gly Ile Leu Pro Gly His Ile Pro Thr Lys Ala Pro Leu Lys Ile Gly
            35                  40                  45

Ala Val Arg Leu Lys Lys Asp Gly Gln Thr Glu Met Val Ala Val Ser
    50                  55                  60

Gly Gly Thr Val Glu Val Arg Pro Asp His Val Thr Ile Asn Ala Gln
65                  70                  75                  80

Ala Ala Glu Thr Ala Glu Gly Ile Asp Lys Glu Arg Ala Glu Ala Ala
                85                  90                  95

Arg Gln Arg Ala Gln Glu Arg Leu Asn Ser Gln Ser Asp Asp Thr Asp
                100                 105                 110

Ile Arg Arg Ala Glu Leu Ala Leu Gln Lys Ala Leu Asn Lys Leu Asp
            115                 120                 125

Val Ala Gly Lys
        130

<210> SEQ ID NO 13
<211> LENGTH: 598
<212> TYPE: PRT
<213> ORGANISM: Artificial Sequence
<220> FEATURE:
<223> OTHER INFORMATION: Synthetic

<400> SEQUENCE: 13

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
                20                  25                  30
```

```
Arg Pro Tyr Glu Gly His Gln Glu Met Thr Leu Arg Val Thr Met Ala
         35                  40                  45

Glu Gly Gly Pro Met Pro Phe Ala Phe Asp Leu Val Ser His Val Phe
 50                  55                  60

Cys Tyr Gly His Arg Val Phe Thr Lys Tyr Pro Glu Glu Ile Pro Asp
 65                  70                  75                  80

Tyr Phe Lys Gln Ala Phe Pro Glu Gly Leu Ser Trp Glu Arg Ser Leu
                 85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Ala Met Lys Thr Val Lys
    210                 215                 220

Val Asn Ile Thr Thr Pro Asp Gly Pro Val Tyr Asp Ala Asp Ile Glu
225                 230                 235                 240

Met Val Ser Val Arg Ala Glu Ser Gly Asp Leu Gly Ile Leu Pro Gly
                245                 250                 255

His Ile Pro Thr Lys Ala Pro Leu Lys Ile Gly Ala Val Arg Leu Lys
            260                 265                 270

Lys Asp Gly Gln Thr Glu Met Val Ala Val Ser Gly Thr Val Glu
        275                 280                 285

Val Arg Pro Asp His Val Thr Ile Asn Ala Gln Ala Ala Glu Thr Ala
    290                 295                 300

Glu Gly Ile Asp Lys Glu Arg Ala Glu Ala Ala Arg Gln Arg Ala Gln
305                 310                 315                 320

Glu Arg Leu Asn Ser Gln Ser Asp Asp Thr Asp Ile Arg Arg Ala Glu
                325                 330                 335

Leu Ala Leu Gln Lys Ala Leu Asn Lys Leu Asp Val Ala Gly Lys Ala
            340                 345                 350

Asp Gly Ser Val Gln Leu Ala Asp His Tyr Gln Gln Asn Thr Pro Ile
        355                 360                 365

Gly Asp Gly Pro Val Leu Leu Pro Asp Asn His Tyr Leu Ser Thr Gln
    370                 375                 380

Ser Lys Leu Ser Lys Asp Pro Asn Glu Lys Arg Asp His Met Val Leu
385                 390                 395                 400

Leu Glu Phe Val Thr Ala Ala Gly Ile Thr Leu Gly Met Asp Glu Leu
                405                 410                 415

Tyr Lys Gly Gly Ser Gly Gly Met Val Ser Lys Gly Glu Glu Leu Phe
            420                 425                 430

Thr Gly Val Val Pro Ile Leu Val Glu Leu Asp Gly Asp Val Asn Gly
        435                 440                 445
```

His Lys Phe Ser Val Ser Gly Glu Gly Glu Gly Asp Ala Thr Tyr Gly
            450                 455                 460

Lys Leu Thr Leu Lys Phe Ile Cys Thr Thr Gly Lys Leu Pro Val Pro
465                 470                 475                 480

Trp Pro Thr Leu Val Thr Thr Leu Thr Tyr Gly Val Gln Cys Phe Ser
                485                 490                 495

Arg Tyr Pro Asp His Met Lys Gln His Asp Phe Phe Lys Ser Ala Met
            500                 505                 510

Pro Glu Gly Tyr Val Gln Glu Arg Thr Ile Phe Phe Lys Asp Asp Gly
            515                 520                 525

Asn Tyr Lys Thr Arg Ala Glu Val Lys Phe Glu Gly Asp Thr Leu Val
530                 535                 540

Asn Arg Ile Glu Leu Lys Gly Ile Asp Phe Lys Glu Asp Gly Asn Ile
545                 550                 555                 560

Leu Gly His Lys Leu Glu Tyr Asn Tyr Asn Ser His Asn Val Tyr Ile
                565                 570                 575

Met Ala Asp Lys Gln Lys Asn Gly Ile Lys Val Asn Phe Lys Ile Arg
            580                 585                 590

His Asn Ile Glu Glu Ala
        595

<210> SEQ ID NO 14
<211> LENGTH: 396
<212> TYPE: DNA
<213> ORGANISM: Artificial Sequence
<220> FEATURE:
<223> OTHER INFORMATION: Synthetic

<400> SEQUENCE: 14
atgaaaactg tgaaagtgaa tataacaacc cctgatgggc cagtctacga cgctgatatc        60
gagatggtgt ccgtgcgggc cgagagtggt gatctcggca tcctcccgg tcacattccc       120 acaaaggccc cactgaagat cggagctgtg cggctgaaga aggacggcca aaccgagatg       180
gtcgcagtct caggcggcac tgttgaagtg cggcctgacc acgttaccat taatgctcaa       240
gccgctgaaa cagccgaagg aatcgacaaa gagagagcag aagccgcaag acagagggcc       300
caggagcggc tgaactctca atccgatgac accgatattc gccgggccga gctggcactg       360
cagagggccc tgaacagact ggacgtggct gggaag                                 396

<210> SEQ ID NO 15
<211> LENGTH: 132
<212> TYPE: PRT
<213> ORGANISM: Artificial Sequence
<220> FEATURE:
<223> OTHER INFORMATION: Synthetic

<400> SEQUENCE: 15

Met Lys Thr Val Lys Val Asn Ile Thr Thr Pro Asp Gly Pro Val Tyr
1               5                   10                  15

Asp Ala Asp Ile Glu Met Val Ser Val Arg Ala Glu Ser Gly Asp Leu
            20                  25                  30

Gly Ile Leu Pro Gly His Ile Pro Thr Lys Ala Pro Leu Lys Ile Gly
        35                  40                  45

Ala Val Arg Leu Lys Lys Asp Gly Gln Thr Glu Met Val Ala Val Ser
    50                  55                  60

Gly Gly Thr Val Glu Val Arg Pro Asp His Val Thr Ile Asn Ala Gln
65                  70                  75                  80

```
Ala Ala Glu Thr Ala Glu Gly Ile Asp Lys Glu Arg Ala Glu Ala Ala
        85                  90                  95

Arg Gln Arg Ala Gln Glu Arg Leu Asn Ser Gln Ser Asp Asp Thr Asp
        100                 105                 110

Ile Arg Arg Ala Glu Leu Ala Leu Gln Lys Ala Leu Asn Lys Leu Asp
        115                 120                 125

Val Ala Gly Lys
        130
```

```
<210> SEQ ID NO 16
<211> LENGTH: 396
<212> TYPE: DNA
<213> ORGANISM: Artificial Sequence
<220> FEATURE:
<223> OTHER INFORMATION: Synthetic

<400> SEQUENCE: 16
atgaaaactg tgaaagtgaa tataacaacc cctgatgggc cagtctacga cgctgatatc      60
gagatggtgt ccgtgcgggc cgagagtggt gatctcggca tcctccccgg tcacattccc     120
acaaaggccc cactgaagat cggagctgtg cggctgaaga aggacggcca aaccgagatg     180
gtcgcagtct caggcggcac tgttgaagtg cggcctgacc acgttaccat taatgctcaa     240
gccgctgaaa cagccgaagg aatcgacaaa gagagagcag aagccgcaag acagagggcc     300
caggagcggc tgaactctca atccgatgac accgatattc gccgggccga gctggcactg     360
cagaaggccc tgaacaagct ggacgtggct gggaag                               396
```

```
<210> SEQ ID NO 17
<211> LENGTH: 1794
<212> TYPE: DNA
<213> ORGANISM: Artificial Sequence
<220> FEATURE:
<223> OTHER INFORMATION: Synthetic

<400> SEQUENCE: 17
atggtgagtg tgattaaacc agagatgaag atgaggtact acatggacgg ctccgtcaat      60
gggcatgagt tcacaattga aggtgaaggc acaggcagac cttacgaggg acatcaagag     120
atgacactac gcgtcacaat ggccgagggc gggccaatgc cttttgcgtt tgacttagtg     180
tcacacgtgt tctgttacgg ccacagagta tttactaaat atccagaaga gataccagac     240
tatttcaaac aagcatttcc tgaaggcctg tcatgggaaa ggtcgttgga gttcgaagat     300
ggtgggtccg cttcagtcag tgcgcatata agccttagag aaacacctt ctaccacaaa     360
tccaaattta ctggggttaa ctttcctgcc gatggtccta tcatgcaaaa ccaaagtgtt     420
gattgggagc catcaaccga gaaaattact gccagcgacg gagttctgaa gggtgatgtt     480
acgatgtacc taaaacttga aggaggcggc aatcacaaat gccaattcaa gactacttac     540
aaggcggcaa agagattct gaaatgcca ggagaccatt acatcggcca tcgcctcgtc     600
aggaaaaccg aaggcaacat tactgagcag gtagaagatg cagtagctca ttccgctatg     660
aaaactgtga agtgaatat aacaacccct gatgggccag tctacgacgc tgatatcgag     720
atggtgtccg tgcgggccga gagtggtgat ctcggcatcc tccccggtca cattcccaca     780
aaggccccac tgaagatcgg agctgtgcgg ctgaagaagg acggccaaac cgagatggtc     840
gcagtctcag gcggcactgt tgaagtgcgg cctgaccacg ttaccattaa tgctcaagcc     900
gctgaaacag ccgaaggaat cgacaaagag agagcagaag ccgcaagaca gagggcccag     960
gagcggctga actctcaatc cgatgacacc gatattcgcc gggccgagct ggcactgcag    1020
```

```
agggccctga acagactgga cgtggctggg aaggctgacg gcagcgtgca gctcgccgac    1080
cactaccagc agaacacccc catcggcgac ggccccgtgc tgctgcccga caaccactac    1140
ctgagcaccc agtccaagct gagcaaagac cccaacgaga agcgcgatca catggtcctg    1200
ctggagttcg tgaccgccgc cgggatcact ctcggcatgg acgagctgta caagggtggc    1260
agcggtggca tggtgagcaa gggcgaggag ctgttcaccg gggtggtgcc catcctggtc    1320
gagctggacg gcgacgtaaa cggccacaag ttcagcgtgt ccggcgaggg cgagggcgat    1380
gccacctacg gcaagctgac cctgaagttc atctgcacca ccggcaagct gcccgtgccc    1440
tggcccaccc tcgtgaccac cctgacctac ggcgtgcagt gcttcagccg ctaccccgac    1500
cacatgaagc agcacgactt cttcaagtcc gccatgcccg aaggctacgt ccaggagcgc    1560
accatcttct tcaaggacga cggcaactac aagacccgcg ccgaggtgaa gttcgagggc    1620
gacaccctgg tgaaccgcat cgagctgaag ggcatcgact tcaaggagga cggcaacatc    1680
ctggggcaca gctggagta caactacaac agccacaacg tctatatcat ggccgacaag    1740
cagaagaacg gcatcaaggt gaacttcaag atccgccaca acatcgagga agct           1794

<210> SEQ ID NO 18
<211> LENGTH: 1794
<212> TYPE: DNA
<213> ORGANISM: Artificial Sequence
<220> FEATURE:
<223> OTHER INFORMATION: Synthetic

<400> SEQUENCE: 18
atggtgagtg tgattaaacc agagatgaag atgaggtact acatggacgg ctccgtcaat      60
gggcatgagt tcacaattga aggtgaaggc acaggcagac cttacgaggg acatcaagag     120
atgacactac gcgtcacaat ggccgagggc gggccaatgc cttgcgcgtt tgacttagtg     180
tcacacgtgt tctgttacgg ccacagagta tttactaaat atccagaaga gataccagac     240
tatttcaaac aagcatttcc tgaaggcctg tcatgggaaa ggtcgttgga gttcgaagat     300
ggtgggtccg cttcagtcag tgcgcatata agccttagag aaacaccttt ctaccacaaa     360
tccaaattta ctggggttaa cttcctgcc gatggtccta tcatgcaaaa ccaaagtgtt     420
gattgggagc catcaaccga gaaaattact gccagcgacg gagttctgaa gggtgatgtt    480
acgatgtacc taaaacttga aggaggcggc aatcacaaat gccaattcaa gactacttac     540
aaggcggcaa agagattct tgaaatgcca ggagaccatt acatcggcca tcgcctcgtc    600
aggaaaaccg aaggcaacat tactgagcag gtagaagatg cagtagctca ttccgctatg     660
aaaactgtga agtgaatat aacaacccct gatgggccag tctacgacgc tgatatcgag     720
atggtgtccg tgcgggccga gagtggtgat ctcggcatcc tccccggtca cattcccaca    780
aaggccccac tgaagatcgg agctgtgcgg ctgaagaagg acggccaaac cgagatggtc     840
gcagtctcag cggcactgt tgaagtgcgg cctgaccacg ttaccattaa tgctcaagcc    900
gctgaaacag ccgaaggaat cgacaaagag agagcagaag ccgcaagaca gagggcccag    960
gagcggctga actctcaatc cgatgacacc gatattcgcc gggccgagct ggcactgcag   1020
aaggccctga caagctgga cgtggctggg aaggctgacg gcagcgtgca gctcgccgac    1080
cactaccagc agaacacccc catcggcgac ggccccgtgc tgctgcccga caaccactac    1140
ctgagcaccc agtccaagct gagcaaagac cccaacgaga agcgcgatca catggtcctg    1200
ctggagttcg tgaccgccgc cgggatcact ctcggcatgg acgagctgta caagggtggc    1260
```

```
agcggtggca tggtgagcaa gggcgaggag ctgttcaccg ggtggtgcc catcctggtc      1320 gagctggacg gcgacgtaaa cggccacaag ttcagcgtgt ccggcgaggg cgagggcgat      1380
gccacctacg gcaagctgac cctgaagttc atctgcacca ccggcaagct gcccgtgccc      1440
tggcccaccc tcgtgaccac cctgacctac ggcgtgcagt gcttcagccg ctaccccgac      1500
cacatgaagc agcacgactt cttcaagtcc gccatgcccg aaggctacgt ccaggagcgc      1560
accatcttct tcaaggacga cggcaactac aagacccgcg ccgaggtgaa gttcgagggc      1620
gacaccctgg tgaaccgcat cgagctgaag ggcatcgact tcaaggagga cggcaacatc      1680
ctggggcaca gcctggagta caactacaac agccacaacg tctatatcat ggccgacaag      1740
cagaagaacg gcatcaaggt gaacttcaag atccgccaca acatcgagga agct            1794
```

<210> SEQ ID NO 19
<211> LENGTH: 598
<212> TYPE: PRT
<213> ORGANISM: Artificial Sequence
<220> FEATURE:
<223> OTHER INFORMATION: Synthetic

<400> SEQUENCE: 19

```
Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Ala Met Lys Thr Val Lys
    210                 215                 220

Val Asn Ile Thr Thr Pro Asp Gly Pro Val Tyr Asp Ala Asp Ile Glu
225                 230                 235                 240

Met Val Ser Val Arg Ala Glu Ser Gly Asp Leu Gly Ile Leu Pro Gly
                245                 250                 255

His Ile Pro Thr Lys Ala Pro Leu Lys Ile Gly Ala Val Arg Leu Lys
            260                 265                 270
```

```
Lys Asp Gly Gln Thr Glu Met Val Ala Val Ser Gly Thr Val Glu
                275                 280                 285

Val Arg Pro Asp His Val Thr Ile Asn Ala Gln Ala Glu Thr Ala
    290                 295                 300

Glu Gly Ile Asp Lys Glu Arg Ala Glu Ala Arg Gln Arg Ala Gln
305                 310                 315                 320

Glu Arg Leu Asn Ser Gln Ser Asp Asp Thr Asp Ile Arg Arg Ala Glu
                325                 330                 335

Leu Ala Leu Gln Lys Ala Leu Asn Leu Asp Val Ala Gly Lys Ala
                340                 345                 350

Asp Gly Ser Val Gln Leu Ala Asp His Tyr Gln Gln Asn Thr Pro Ile
                355                 360                 365

Gly Asp Gly Pro Val Leu Leu Pro Asp Asn His Tyr Leu Ser Thr Gln
370                 375                 380

Ser Lys Leu Ser Lys Asp Pro Asn Glu Lys Arg Asp His Met Val Leu
385                 390                 395                 400

Leu Glu Phe Val Thr Ala Ala Gly Ile Thr Leu Gly Met Asp Glu Leu
                405                 410                 415

Tyr Lys Gly Gly Ser Gly Gly Met Val Ser Lys Gly Glu Glu Leu Phe
                420                 425                 430

Thr Gly Val Val Pro Ile Leu Val Glu Leu Asp Gly Asp Val Asn Gly
            435                 440                 445

His Lys Phe Ser Val Ser Gly Glu Gly Glu Gly Asp Ala Thr Tyr Gly
            450                 455                 460

Lys Leu Thr Leu Lys Phe Ile Cys Thr Thr Gly Lys Leu Pro Val Pro
465                 470                 475                 480

Trp Pro Thr Leu Val Thr Thr Leu Thr Tyr Gly Val Gln Cys Phe Ser
                485                 490                 495

Arg Tyr Pro Asp His Met Lys Gln His Asp Phe Phe Lys Ser Ala Met
                500                 505                 510

Pro Glu Gly Tyr Val Gln Glu Arg Thr Ile Phe Phe Lys Asp Asp Gly
                515                 520                 525

Asn Tyr Lys Thr Arg Ala Glu Val Lys Phe Glu Gly Asp Thr Leu Val
530                 535                 540

Asn Arg Ile Glu Leu Lys Gly Ile Asp Phe Lys Glu Asp Gly Asn Ile
545                 550                 555                 560

Leu Gly His Lys Leu Glu Tyr Asn Tyr Asn Ser His Asn Val Tyr Ile
                565                 570                 575

Met Ala Asp Lys Gln Lys Asn Gly Ile Lys Val Asn Phe Lys Ile Arg
                580                 585                 590

His Asn Ile Glu Glu Ala
        595

<210> SEQ ID NO 20
<211> LENGTH: 4
<212> TYPE: PRT
<213> ORGANISM: Artificial Sequence
<220> FEATURE:
<223> OTHER INFORMATION: Synthetic

<400> SEQUENCE: 20

Pro Pro Pro Pro
1

<210> SEQ ID NO 21
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 21

Gly Thr Ser Gly
1

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Ala Asn Glu Phe Met
1               5
```

METHODS AND COMPOSITIONS FOR LIVE CELL ANALYSIS OF INTRACELLULAR ATP

CROSS REFERENCE

This application is a U.S. national phase of International Application No. PCT/US2019/021171, filed on Mar. 7, 2019, which claims priority to U.S. Provisional Application No. 62/640,983, filed Mar. 9, 2018, both of which are incorporated by reference herein in their entirety.

BACKGROUND

Standard approaches to monitoring drug induced metabolic perturbations are limited to endpoint assays that provide population-based measurements and limited kinetic information. A genetically encoded ATP sensor that enables direct, automated live cell analysis of cellular ATP levels is provided according to aspects of the present disclosure along with methods of use.

SUMMARY

In one aspect fusion proteins are disclosed, comprising a polypeptide of genus X1-X2-X3-X4-X5, wherein:
one of X1 and X5 comprises a fluorescence resonance energy transfer (FRET) acceptor polypeptide having an acceptor excitation wavelength and FRET emission wavelength, and the other of X1 and X5 comprises a FRET donor polypeptide having a donor excitation wavelength and a donor emission wavelength
X2 and X4 independently are optional amino acid linkers; and
X3 comprises an ATP binding protein;
wherein binding of ATP by the ATP binding protein causes interaction of the FRET acceptor polypeptide and the FRET donor polypeptide.

In one embodiment, X1 comprises a FRET acceptor polypeptide and X5 comprises a FRET donor polypeptide; in another embodiment, X1 comprises a FRET donor polypeptide and X5 comprises a FRET acceptor polypeptide. In various embodiments, X2 is an amino acid linker of between 1-2 amino acids in length, or is absent. In other embodiments, X2 is an amino acid linker selected from the group consisting of A, S, P, V, T, TS, ID, or wherein X2 is absent. In further embodiments, X4 is an amino acid linker of between 1-5 amino acids in length, or wherein X4 is absent. In other embodiments, X4 is an amino acid linker selected from the group consisting of AT, A, SA, GA, FF, PPPP (SEQ ID NO: 20), FL, GTSG (SEQ ID NO: 21), P, S, ANEFM (SEQ ID NO: 22), or wherein X4 is absent. In various embodiments X2 and X4 are both A; X2 is S and X4 is A;
X2 is absent and X4 is FF; X2 is V and X4 is FL; X2 is T and X4 is GTSG (SEQ ID NO: 21); or X2 is S and X4 is SA. In another embodiment, X2 and X4 do not include any proline residues. In other embodiments, the FRET acceptor polypeptide has a maximal acceptor excitation wavelength in a range of 500 to 560 nm and an acceptor maximal emission wavelength in a range of 530 to 580 nm. In further embodiments, the FRET acceptor polypeptide comprises an amino acid sequence at least 90%, 91%, 92%, 93%, 94% 95%, 96%, 97%, 98%, 99%, or 100% identical along the length of the amino acid sequence of one or more of SEQ ID NOs:1-3 and identical at the chromophore. In another embodiment, all optional amino acid residues in the FRET acceptor polypeptide are present. In one embodiment, the FRET donor polypeptide has a maximal donor excitation wavelength in a range of 450 to 500 nm and a maximal donor emission wavelength in a range of 480 to 515 nm. In other embodiments, the FRET donor polypeptide comprises an amino acid sequence at least 85%, 87%, 90%, 91%, 92%, 93%, 94% 95%, 96%, 97%, 98%, 99%, or 100% identical along the length of the amino acid sequence of SEQ ID NO: 4 and identical at the chromophore. In further embodiments, X3 comprises an ATP binding protein comprising the amino acid sequence at least 65%, 67%, 68%, 70%, 75%, 80%, 85%, 90%, 91%, 92%, 93%, 94% 95%, 96%, 97%, 98%, 99%, or 100% identical along the length of the amino acid sequence selected from the group consisting of SEQ ID NOS:5-6. In another embodiment, the fusion protein comprises an amino acid sequence at least 90%, 91%, 92%, 93%, 94% 95%, 96%, 97%, 98%, 99%, or 100% identical along the length of the amino acid sequence selected from the group consisting of SEQ ID NOS:7-11.

In another aspect, control fusion proteins are disclosed, that include all embodiments and combination of embodiments of the fusion proteins and components thereof disclosed herein, except that X3 comprises a control protein that does not bind to ATP. In one embodiment, X3 comprises an amino acid sequence at least 65%, 67%, 68%, 70%, 75%, 80%, 85%, 90%, 91%, 92%, 93%, 94% 95%, 96%, 97%, 98%, 99%, or 100% identical along the length of the amino acid sequence of SEQ ID NO:12, wherein the underlined and bold font residues in SEQ ID NO:12 must be K. In other embodiments, the control fusion proteins comprises an amino acid sequence at least 65%, 67%, 68%, 70%, 75%, 80%, 85%, 90%, 91%, 92%, 93%, 94% 95%, 96%, 97%, 98%, 99%, or 100% identical along the length of the amino acid sequence of SEQ ID NO:13, wherein the underlined and bold font residues in SEQ ID NO:13 must be K.

In a further aspect, polynucleotides are disclosed that encode the fusion protein or control protein of any embodiment or combination of embodiments disclosed herein. In other aspects, the disclosure provides expression vectors encoding the polynucleotides of the disclosure, wherein the polynucleotide is operatively linked to a promoter sequence capable of directing expression of the polynucleotide, and recombinant host cells comprising the polynucleotides or expression vectors of any embodiment or combination of embodiments disclosed herein. In one embodiment, the host cell is a cell of a stable transformant cell line.

In further aspects, the disclosure provides kits comprising one or more fusion protein and one or more control fusion protein of any embodiment or combination of embodiments disclosed herein. In another aspect, the disclosure provides methods for use of the fusion proteins for determining a level of ATP in a cell of interest. In one embodiment, the method of assaying ATP, comprises:
(a) expressing the fusion protein of any embodiment or combination of embodiments disclosed herein in one or more first cells, and generating one or more images selected from the group consisting of:
(i) a first fluorescence image generated by detecting fluorescent signals produced by light having the FRET acceptor polypeptide emission wavelength emitted from the one or more first cells upon exposing the one or more first cells to light having the FRET donor polypeptide excitation wavelength; and/or
(ii) a second fluorescence image generated by detecting fluorescent signals produced by light having the FRET acceptor polypeptide emission wavelength emitted from the one or more first cells upon exposing the one or more first cells to light having the FRET acceptor polypeptide excitation wavelength; and/or (iii) a third fluorescence image generated by detecting fluorescent signals produced by light having the FRET donor polypeptide emission wavelength emitted from the one or more first cells upon exposing the one or more first cells to light having the FRET donor polypeptide excitation wavelength; and (b) determining a FRET ratio in the one or more first cells by comparing the output of fluorescent signals in the first fluorescent image, the second fluorescent image, and/or the third fluorescent image;

wherein the level of ATP in the one or more first cells is proportional to the determined FRET ratio. In one embodiment, the methods further comprises expressing the control fusion protein of any embodiment or combination of embodiments disclosed herein in one or more first cells, and detecting a control signal produced by light having the acceptor emission wavelength emitted from the one or more first cells. In one embodiment, detecting the control signal comprises (c) expressing the control fusion protein of any embodiment or combination of embodiments disclosed herein in one or more control cells (such as the first cells, or second cells), and generating one or more images selected from the group consisting of:

(i) a fourth fluorescence image generated by detecting fluorescent signals produced by light having the FRET acceptor polypeptide emission wavelength emitted from the one or more control cells upon exposing the one or more control cells to light having the FRET donor polypeptide excitation wavelength; and/or (ii) a fifth fluorescence image generated by detecting fluorescent signals produced by light having the FRET acceptor polypeptide emission wavelength emitted from the one or more control cells upon exposing the one or more control cells to light having the FRET acceptor polypeptide excitation wavelength; and/or (iii) a sixth fluorescence image generated by detecting fluorescent signals produced by light having the FRET donor polypeptide emission wavelength emitted from the one or more control cells upon exposing the one or more control cells to light having the FRET donor polypeptide excitation wavelength; and (d) determining a control fusion FRET ratio in the one or more control cells by comparing the output of fluorescent signals in the fourth fluorescent image, the fifth fluorescent image, and/or the sixth fluorescent image;

wherein alterations in the control fusion FRET ratio are determined to be the result of experimental conditions unrelated to ATP binding, and wherein the determined FRET ratio is corrected based on the alterations in the control fusion FRET ratio.

In a further embodiment, the one or more first cells are in culture in an incubator, wherein all imaging steps are performed without removing the one or more first cells from the incubator. In another embodiment, the method further comprises contacting the one or more first cells with one or more test substance and determining an effect of the test substance on the presence of ATP in the one or more first cells. In another embodiment, the effect of the one or more test substance on the presence of ATP in the one or more first cells is determined continuously or intermittently over a time period in the range of 1 minute to three months.

In another aspect the disclosure provides polynucleotides encoding a fusion protein, as well as the fusion proteins themselves, the fusion protein comprising: a first fluorophore that is a FRET acceptor having an acceptor excitation wavelength and a FRET emission wavelength, the first fluorophore having an N-terminus and a C-terminus; an ATP binding protein having an N-terminus and a C-terminus; and a second fluorophore that is a FRET donor having a donor excitation wavelength and donor emission wavelength, the second fluorophore having an N-terminus and a C-terminus, wherein a first linker is disposed between the C-terminus of the first fluorophore and the N-terminus of the ATP binding protein and a second linker is disposed between the C-terminus of the ATP binding protein and the N-terminus of the second fluorophore, and wherein the first fluorophore, ATP binding protein, and second fluorophore are operably linked such that binding of ATP by the ATP binding protein causes interaction of the first fluorophore and second fluorophore to produce a FRET emission signal when exposed to light having the donor excitation wavelength. In other embodiments, the polynucleotide further comprises an operably linked promoter; the polynucleotide is comprised in an expression vector; and host cells comprising the polynucleotide or the expression vector are disclosed.

DETAILED DESCRIPTION

Figure 1:
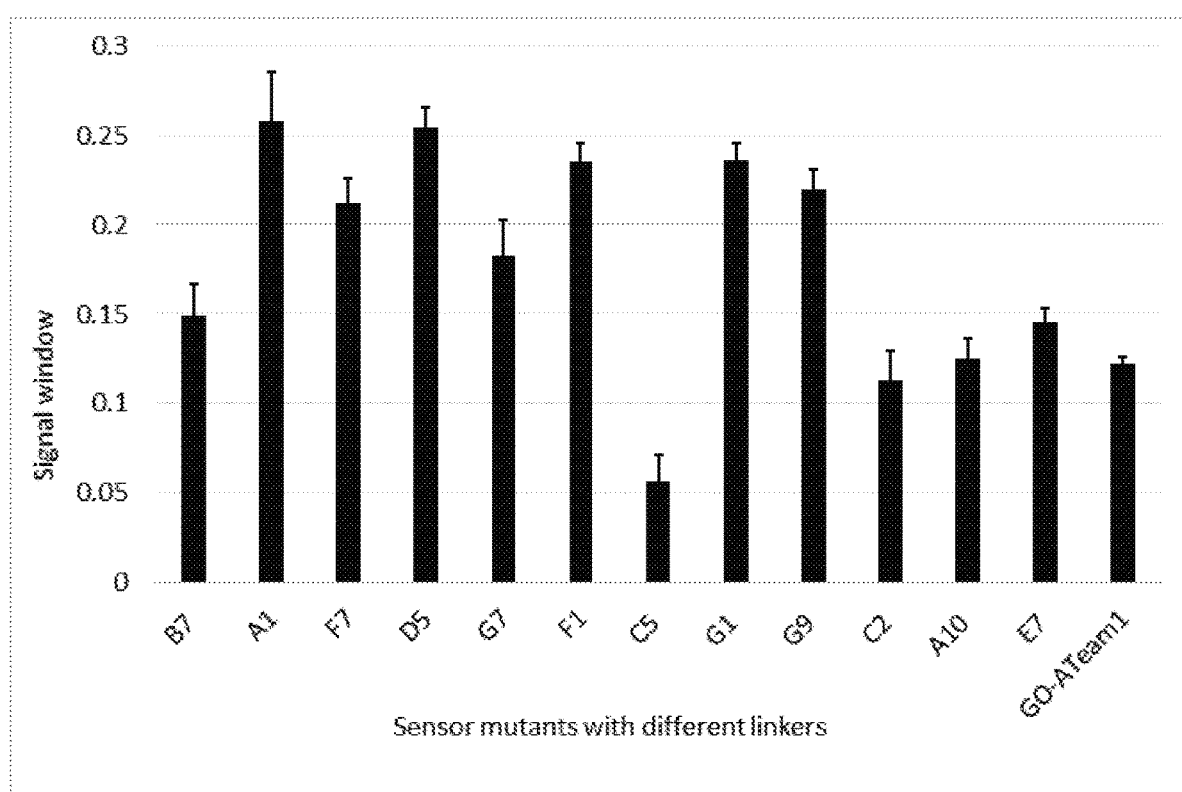
FIG. 1 is a graphical representation of signal window calculated for exemplary fusion proteins of the disclosure by subtracting the FRET ratio of drug-treated cells from the FRET ratio of the vehicle-treated cells 2 h post treatment.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and MM. Cox, Lehninger Principles of Biochemistry, 4th Ed., W. H. Freeman & Company, 2004; and Herdewijn, P. (Ed.), Oligonucleotide Synthesis: Methods and Applications, Methods in Molecular Biology, Humana Press, 2004.

The singular terms "a," "an," and "the" are not intended to be limiting and include plural referents unless explicitly stated otherwise or the context clearly indicates otherwise.

All embodiments disclosed herein can be combined unless the context clearly indicates otherwise.

In a first aspect, the disclosure provides fusion proteins, comprising a polypeptide of genus X1-X2-X3-X4-X5, wherein:
- one of X1 and X5 comprises a fluorescence resonance energy transfer (FRET) acceptor polypeptide having an acceptor excitation wavelength and FRET emission wavelength, and the other of X1 and X5 comprises a FRET donor polypeptide having a donor excitation wavelength and a donor emission wavelength
- X2 and X4 independently are optional amino acid linkers; and
- X3 comprises an ATP binding protein;
- wherein binding of ATP by the ATP binding protein causes interaction of the FRET acceptor polypeptide and the FRET donor polypeptide.

The fusion proteins of this first aspect can be used, for example, to detect and measure ATP in living cells, as detailed in the examples that follow.

Fluorescence Resonance Energy Transfer (FRET) is non-radiative transfer of energy from an excited donor fluorophore to a suitable acceptor fluorophore in proximity to the donor. For selection of FRET fluorophore donor/acceptor polypeptide pairs for use in the fusion proteins of the disclosure, the absorption and emission wavelengths of each are considered. Based on the teachings herein, one of skill in the at can readily determine which of various fluorophores are to be used as FRET donor/acceptor polypeptide pairs in a particular application.

In one embodiment, X1 comprises a FRET acceptor polypeptide and X5 comprises a FRET donor polypeptide; in another embodiment, X1 comprises a FRET donor polypeptide and X5 comprises a FRET acceptor polypeptide.

Any suitable polypeptide fluorophores may be used, including but not limited to, any of green fluorescent protein and derivatives such as BFP, EBFP, EBFP2, ECFP, RFP, and YFP, and other polypeptide fluorophores described herein.

In another embodiment, the FRET acceptor polypeptide has a maximal acceptor excitation wavelength in a range of 500 to 560 nm and an acceptor maximal emission wavelength in a range of 530 to 580 nm. In another embodiment as described in the examples that follow, the FRET acceptor polypeptide comprises an amino acid sequence at least 90%, 91%, 92%, 93%, 94% 95%, 96%, 97%, 98%, 99%, or 100% identical along the length of the amino acid sequence of one or more of SEQ ID NOs:1-3 and identical at the chromophore (noted by highlighted residues). Residues in parentheses are optional throughout.

```
mKOk
                                              (SEQ ID NO: 1)
(MVSVI)KPEMKMRYYMDGSVNGHEFTIEGEGTGRPYEGHQEMTLRVTMA

EGGPMPFAFDLVSHVFCYGHRVFTKYPEEIPDYFKQAFPEGLSWERSLEF

EDGGSASVSAHISLRGNTFYHKSKFTGVNFPADGPIMQNQSVDWEPSTEK

ITASDGVLKGDVTMYLKLEGGGNHKCQFKTTYKAAKEILEMPGDHYIGHR

LVRKTEGNITEQVEDAVA(HS)

mKO
                                              (SEQ ID NO: 2)
(MSVIK)PEMKKRYYMDGSVNGHEFTIEGEGTGRPYEGHQEMTLRVTMAK

GGPMPFAFDLVSHVFCYGHRPFTKYPEEIPDYFKQAFPEGLSWERSLEFE

DGGSASVSAHISLRGNTFYHKSKFTGVNFPADGPIMQNQSVDWEPSTEKI

TASDGVLKGDVTMYLKLEGGGNHKCQFKTTYKAAKKILKMPGSHYISHRL

VRKTEGNITELVEDAVA(HS)

mKO2
                                              (SEQ ID NO: 3)
(MVSVI)KPEMKMRYYMDGSVNGHEFTIEGEGTGRPYEGHQEMTLRVTMA

EGGPMPFAFDLVSHVFCYGHRVFTKYPEEIPDYFKQAFPEGLSWERSLEF

EDGGSASVSAHISLRGNTFYHKSKFTGVNFPADGPIMQNQSVDWEPSTEK

ITASDGVLKGDVTMYLKLEGGGNHKCQMKTTYKAAKEILEMPGDKYIGHR

LVRKTEGNITEQVEDAVA(HS)
```

In one embodiment, all optional amino acid residues in the FRET acceptor polypeptide are present.

In another embodiment, the FRET donor polypeptide has a maximal donor excitation wavelength in a range of 450 to 500 nm and a maximal donor emission wavelength in a range of 480 to 515 nm. In another embodiment as described in the examples that follow, the FRET donor polypeptide comprises an amino acid sequence at least 85%, 87%, 90%, 91%, 92%, 93%, 94% 95%, 96%, 97%, 98%, 99%, or 100% identical along the length of the amino acid sequence of SEQ ID NO: 4 and identical at the chromophore (highlighted residues).

```
Circularly permuted (cpm) ECFP:
                                             SEQ ID. NO: 4
(DG)SVQLADKYQQNTPIGDGFVLLPDNHYLSTQS(A/K)LSKDPNEKRD

HMVLLEFVTAAGITLGMDELYKGGSGGMVSKGEELFTGVVPILVELDGDV

NGHKFSVSGEGEGDATYGKLTLKFICTTGKLPVPWPTLVTTLTYGVQCFS

RYPDKMKQHDFFKSAMPEGYVQERTIFFKDDGNYKTRAEVKFEGDTLVNR

IELKGIDFKEDGNILGHKLEYNYNSHNVYIMADKQKNGIKVNFKIRHNIE (EA)
```

Exemplary FRET donor polypeptides having the requisite amino acid sequence identity to SEQ ID NO:4 and which can be used in the fusion proteins of the disclosure are listed in Table 1 below.

TABLE 1

| Name | % Identity to SEQ ID NO: 4 | Database accession # |
|---|---|---|
| M1S2 protein [synthetic construct] | 97% | gi\|400653667\|AFP87541.1 |
| PKG#6 [synthetic construct] | 98% | gi\|1033838710\|ANH79566.1 |
| PKG#8 [synthetic construct] | 98% | gi\|1033838714\|ANH79568.1 |
| NES-YC3.6 [Binary expression vector NES-YC3.6] | 96% | gi\|378792854\|AFC41195.1 |
| yellow cameleon 2.60 [synthetic construct] | 96% | gi\|50507914\|BAD30083.1 |
| yellow cameleon 4.60 [synthetic construct] | 96% | gi\|50507918\|BAD30085.1 |
| yellow cameleon 3.60 [synthetic construct] | 96% | gi\|50507916\|BAD30084.1 |
| YC3.6 [Binary expression vector YC3.6-C] | 96% | gi\|378792870\|AFC41207.1 |
| yellow cameleon Nano50 [synthetic construct] | 96% | gi\|302375510\|ADL29888.1 |
| Fluorescent Mg2+ indicator [synthetic construct] | 96% | gi\|1341117861\|BBC69164.1 |
| calcium sensor cameleon D2cpv [synthetic construct] | 96% | gi\|94471595\|ABF21065.1 |
| yellow cameleon X 2.60 [synthetic construct] | 96% | gi\|765098779\|BAQ56021.1 |
| calcium sensor cameleon D3cpv [synthetic construct] | 96% | gi\|94471597\|ABF21066.1 |
| yellow cameleon Nano15 [synthetic construct] | 96% | gi\|302375506\|ADL29886.1 |
| yellow cameleon Nano30 [synthetic construct] | 96% | gi\|302375508\|ADL29887.1 |
| YC3.6 [Binary expression vector YC3.6-N] | 96% | ai\|378792874\|AFC41210.1 |
| NLS-YC3.6 [Binary expression vector NLS-YC3.6] | 96% | gi\|378792858\|AFC41198.1 |
| yellow cameleon Nano140 [synthetic construct] | 96% | gi\|302375514\|ADL29890.1 |
| yellow cameleon Nano65 [synthetic construct] | 96% | gi\|302375512\|ADL29889.1 |
| calcium sensor cameleon lynD3cpv [synthetic construct] | 96% | gi\|94471601\|ABF21068.1 |
| calcium sensor cameleon D4cpv [synthetic construct] | 96% | gi\|94471599\|ABF21067.1 |
| yellow cameleon Nano50 | 96% | gi\|997831445\|BAU51804.1 |
| yellow cameleon 3.60-pm [synthetic construct] | 96% | gi\|50507920\|BAD30086.1 |
| PKG#7 [synthetic construct] | 96% | gi\|1033838712\|ANH79567.1 |
| PKG#2 [synthetic construct] | 96% | gi\|1033838702\|ANH79562.1 |
| yellow cameleon Nano15 [Cloning vector pLN-YC Nano15] | 96% | gi\|997831443\|BAU51803.1 |
| TP-D3cpv [Binary expression vector TP-D3cp] | 96% | gi\|378792866\|AFC41204.1 |
| PKG#4 [synthetic construct] | 96% | gi\|1033838706\|ANH79564.1 |
| photoactivatable calcium indicator PA-TNXL [ | 96% | gi\|464095426\|BAN00003.1 |
| PM-YC3.6-Lti6b [Binary expression vector PM-YC3.6-LTI6b] | 96% | gi\|378792862\|AFC41201.1 |
| mitochondrial calcium sensor cameleon 4mtD3cpv | 96% | gi\|94471603\|ABF21069.1 |
| 3x GFP [Cloning vector pGGC025] | 93% | gi\|568816479\|AHE38517.1 |
| SV40-3xeGFP [Cloning vector pPLV04] | 97% | gi\|334085767\|AEG42740.1 |
| calcium indicator TN-XXL [synthetic construct] | 95% | gi\|194716543\|ACF93133.1 |
| three repeats of Citrine with GGSGGS linkers | 96% | gi\|929652476\|BAS49686.1 |
| PKG#3 [synthetic construct] | 95% | gi\|1033838704\|ANH79563.1 |
| Twitch-2B [synthetic construct] | 94% | gi\|568402376\|AHD25944.1 |
| mVenus(L68V)-mTurquoise [synthetic construct] | 91% | gi\|341940080\|AEL12177.1 |
| GEPRA-G [synthetic construct] | 93% | gi\|478246796\|BAN14786.1 |
| NLS-YFP-CFP [Yeast integrative vector pBS42] | 93% | gi\|544370144\|AGW21605.1 |
| NLS-YFP-Pro10-CFP [Yeast integrative vector pBS47] | 91% | gi\|544370160\|AGW21617.1 |
| ratiometric fluorescent temperature indicator | 87% | gi\|1177648317\|BAX25172.1 |
| NLS-YFP-Pro15-CFP [Yeast integrative vector pBS48] | 89% | gi\|544370164\|AGW21620.1 |
| NLS-YFP-Pro5-CFP [Yeast integrative vector pBS46] | 92% | gi\|544370156\|AGW21614.1 |
| NLS-YFP-Pro20-CFP [Yeast integrative vector pBS50] | 87% | gi\|544370172\|AGW21626.1 |
| NLS-YFP × CFP [Yeast integrative vector pBS42BN] | 92% | gi\|544370148\|AGW21608.1 |
| MT1-MMP FRET probe protein [synthetic construct] | 88% | gi\|170791211\|ACB38271.1 |
| ssrA-tagged green fluorescent protein [synthetic construct] | 93% | gi\|339905310\|AEK24782.1 |
| photoconvertible fluorescent protein Phamret | 90% | gi\|187370622\|BAG31927.1 |
| calcium-sensing GFP analog [synthetic construct] | 99% | gi\|29150153\|CAD79597.1 |
| MolyProbe protein [synthetic construct] | 96% | ai\|457866284\|BAM93494.1 |
| His-6-tagged G-CaMP1.6 [synthetic construct] | 98% | gi\|94411311\|ABF18599.1 |
| G-CaMP2 [synthetic construct] | 98% | gi\|87248062\|ABD36085.1 |
| GCaMP3 [synthetic construct] | 97% | gi\|299818413\|ADJ53338.1 |
| dLight1.4 [synthetic construct] | 97% | gi\|1398286563\|AWS21700.1 |
| GAP43-GCaMP6s [pAAV-hSyn1-FLEx-GAP43-GCaMP6s] | 97% | gi\|1442830696\|AXK50352.1 |
| GAP43-GCaMP6m [pAAV-hSyn1-GAP43-GCaMP6m] | 97% | gi\|1442830702\|AXK50356.1 |
| GAP43-GCaMP6f [Vector pAAV-hSyn1-GAP43-GCaMP6f] | 97% | gi\|1442830699\|AXK50354.1 |
| dLight1.5 [synthetic construct] | 97% | gi\|1398286565\|AWS21701.1 |
| 5htLight1.1 [synthetic construct] | 97% | gi\|1398286577\|AWS21707.1 |
| G-GECO1 [synthetic construct] | 96% | gi\|345787073\|AEO16868.1 |
| dLight1.1 [synthetic construct] | 97% | gi\|1398286555\|AWS21696.1 |
| dLight1.2 [synthetic construct] | 97% | gi\|1398286557\|AWS21697.1 |
| dLight1.3a [synthetic construct] | 97% | gi\|1398286559\|AWS21698.1 |
| dLight1,3b [synthetic construct] | 97% | gi\|1398286561\|AWS21699.1 |
| glutatmate sensor SF-iGluSnFR [synthetic construct] | 95% | gi\|1488571045\|AYH52532.1 |
| glutatmate sensor SF-iGluSnFR [synthetic construct] | 95% | gi\|1488571043\|AYH52531.1 |
| glutatmate sensor SF-iGluSnFR [synthetic construct] | 95% | gi\|1488571041\|AYH52530.1 |
| nLight3.1 [synthetic construct] | 97% | gi\|1398286571\|AWS21704.1 |
| GEX-GECO [synthetic construct] | 96% | gi\|345786981\|AEO16865.1 |
| iGABA sensor nFR [synthetic construct] | 95% | gi\|1488571039\|AYH52529.1 |
| kLight1.1 [synthetic construct] | 97% | gi\|1398286573\|AWS21705.1 |
| mtLight1.1 [synthetic construct] | 97% | gi\|1398286579\|AWS21708.1 |
| iGABA sensor nFR [synthetic construct] | 95% | gi\|1488571035\|AYH52527.1 |
| iGABA sensor nFR [synthetic construct] | 95% | gi\|1488571037\|AYH52528.1 |
| Crystal Structure Calcium Bound Dimeric Gcamp2 (#2) | 96% | gi\|1209040728\|3EVV_A |
| mLight1.1 [synthetic construct] | 97% | gi\|1398286575\|AWS21706.1 |

TABLE 1-continued

| Name | % Identity to SEQ ID NO: 4 | Database accession # |
|---|---|---|
| ssrA-tagged green fluorescent protein [synthetic construct] | 93% | gi|339905308|AEK24781.1 |
| G-GECO1.1 [synthetic construct] | 96% | gi|345787100|AEO16869.1 |
| Chain A, Crystal Structure Of Circular-permutated Egfp | 96% | gi|217035443|3EVP_A |
| nLight2.1 [synthetic construct] | 97% | gi|1398286569|AWS21703.1 |
| nLight1.1 [synthetic construct] | 97% | gi|1398286567|AWS21702.1 |
| G-CaMP6 protein [synthetic construct] | 96% | gi|815006828|AKE44624.1 |
| G-CaMP7 protein [synthetic construct] | 96% | gi|815006830|AKE44625.1 |
| GCaMP7a [synthetic construct] | 96% | gi|446512552|BAM78547.1 |
| GEM-GECO1 [synthetic construct] | 96% | gi|345786945|AEO16864,1 |
| G-CaMP-HS protein [synthetic construct] | 96% | gi|815006836|AKE44628.1 |
| calcium-sensing GFP protein [synthetic construct] | 96% | gi|335060646|AEH27627.1 |
| Crystal structure of Calcium bound monomeric GCAMP2 | 96% | ai|217035444|3EVR_A |
| G-CaMP4.1 protein [synthetic construct] | 96% | gi|810222674|AKE14367.1 |
| G-CaMP8 protein [synthetic construct] | 95% | gi|815006832|AKE44626.1 |
| G-GECO1.2 [synthetic construct] | 95% | gi|345787127|AEO16870.1 |
| Crystal structure of Calcium bound dimeric GCAMP2 | 96% | gi|217035445|3EVU_A |
| Myosin light chain kinase, GFP, Calmodulin-1 chimera | 96% | gi|392311568|3SG6_A |
| Calcium-free GCaMP2 (calcium binding deficient mutant) | 96% | gi|218681839|3EKJ_A |
| Chain A, High Resolution Structure Of Delta-rest-gcamp3 | 96% | gi|576865036|4IK5_A |
| GCaMP6s-P2A-mKate2 | 97% | gi|1442830714|AXK50364.1 |
| GAP43-GCaMP6s-P2A-mKate2 | 97% | gi|1442830705|AXK50358.1 |
| GCaMP6s-P2A-mRuby3 | 97% | gi|1442830717|AXK50366.1 |
| Chain A, High Resolution Structure Of Gcampj At Ph 8.5 | 96% | gi|582045214|4IK1_A |

Any suitable ATP binding protein can be used in the fusion proteins as deemed appropriate for an intended use (i.e.: capable of being expressed in the cell type to be assayed, etc.) In one non-limiting embodiment as described in the examples that follow, X3 comprises an ATP binding protein comprising the amino acid sequence at least 65%, 67%, 68%, 70%, 75%, 80%, 85%, 90%, 91%, 92%, 93%, 94%, 95%, 96%, 97%, 98%, 99%, or 100% identical along the length of the amino acid sequence selected from the group consisting of SEQ ID NO:5-6 (residues in parentheses are optional).

SEQ ID NO: 5: Modified ε subunit of *Bacillus subtilis* F$_o$F$_1$-ATP synthase
(M)KTVKVNITTPDGPVYDADIEMVSVRAESGDLGILPGHIPTKAPLKIG

AVRLKKDGQTEMVAVSGGTVEVRPDHVTINAQAAETAEGIDKERAEAARQ

RAQERLNSQSDDTDIRRAELALQRALNRLDVAGK

SEQ ID NO: 6 Modified ε subunit of *Bacillus subtilis* F$_o$F$_1$-ATP synthase having two elements from e subunit of *Bacillus* sp. PS3 F$_o$F$_1$-ATP synthase, M to Y mutation and GK to EMK substitution (in bold)
(M)KTVKVNITTPDGPVYDADIEMVSVRAESGDLGILPGHIPTKAPLKIG

AVRLKKDGQTEYVAVSGGTVEVRPDHVTINAQAAETAEGIDKERAEAARQ

RAQERLNSQSDDTDIRRAELALQRALNRLDVAEMK

Exemplary ATP binding proteins having the requisite amino acid sequence identity to SEQ ID NO:5-6 and which can be used in the fusion proteins of the disclosure are listed in Table 2 below.

TABLE 2

MULTISPECIES: ATP synthase epsilon chain [*Bacillus*], 97%, gi|489320353|WP_003227688.1
ATP synthase epsilon chain [*Bacillus subtilis*], 96%, gi|505296717|WP_015483819.1
MULTISPECIES: F0F1 ATP synthase subunit epsilon [*Bacillus*], 96%, gi|504291152|WP_014478254.1
ATP synthase epsilon chain [*Bacillus tequilensis*], 95%, gi|639655008|WP_024713798.1
MULTISPECIES: F0F1 ATP synthase subunit epsilon [*Bacillus*], 95%, gi|545118192|WP_021480810.1
F0F1 ATP synthase subunit epsilon [*Bacillus* sp. FMQ74], 95%, gi|1102032633|WP_071577657.1
MULTISPECIES: F0F1 ATP synthase subunit epsilon [*Bacillus*], 95%, gi|1280952059|WP_100275394.1
MULTISPECIES: F0F1 ATP synthase subunit epsilon [*Bacillus subtilis* group], 95%, gi|1039477827|WP_064816018.1
F0F1 ATP synthase subunit epsilon [*Bacillus subtilis*], 94%, gi|1207627978|WP_087992693.1
MULTISPECIES: F0F1 ATP synthase subunit epsilon [*Bacillus*], 94%, gi|745781482|WP_039075208.1
MULTISPECIES: F0F1 ATP synthase subunit epsilon [*Bacillus*], 92%, gi|498018072|WP_010332228.1
F0F1 ATP synthase subunit epsilon [*Bacillus halotolerans*], 92%, gi|570758358|WP_024123161.1
MULTISPECIES: F0F1 ATP synthase subunit epsilon [*Bacillus subtilis* group], 89%, gi|489420817|WP_003326558.1
MULTISPECIES: ATP synthase epsilon chain [*Bacillus*], 87%, gi|1489242972|WP_003151176.1

TABLE 2-continued

F0F1 ATP synthase subunit epsilon [*Bacillus nakamurai*], 86%, gi|1004344994|WP_061522539.1
MULTISPECIES: ATP synthase F0F1 subunit epsilon [*Bacillus*], 86%, gi|921995573|WP_053285344.1
MULTISPECIES: F0F1 ATP synthase subunit epsilon [*Bacillus*], 86%, gi|740674878|WP_038460167.1
MULTISPECIES: ATP synthase epsilon chain [*Bacillus*], 86%, gi|723597160|WP_033574395.1
MULTISPECIES: ATP synthase epsilon chain [*Bacillus*], 85%, gi|503119226|WP_013353907.1
F0F1 ATP synthase subunit epsilon [*Bacillus velezensis*], 86%, gi|1207676870|WP_088037238.1
MULTISPECIES: F0F1 ATP synthase subunit epsilon [Bacillales], 95%, gi|489314501|WP_003221882.1
F0F1 ATP synthase subunit epsilon [*Bacillus swezeyi*], 82%, gi|1140910370|WP_076759287.1
MULTISPECIES: F0F1 ATP synthase subunit epsilon [*Bacillus*], 82%, gi|651594109|WP_026589081.1
MULTISPECIES: F0F1 ATP synthase subunit epsilon [*Bacillus*], 82%, gi|489278336|WP_003186004.1
F0F1 ATP synthase subunit epsilon [*Bacillus sonorensis*], 82%, gi|493689352|WP_006639406.1
MULTISPECIES: F0F1 ATP synthase subunit epsilon [Bacillales], 82%, gi|521288986|WP_020453254.1
MULTISPECIES: F0F1 ATP synthase subunit epsilon [*Bacillus*], 82%, gi|806497211|WP_046130316.1
F0F1 ATP synthase subunit epsilon [*Bacillus glycinifennentans*], 81%, gi|860247715|WP_048355651.1
ATP synthase subunit epsilon [*Bacillus subtilis* XF-1], 95%, gi|449030049|AGE65288.1
F0F1 ATP synthase subunit epsilon [*Bacillus gobiensis*], 75%, gi|926266349|WP_053604535.1
F0F1 ATP synthase subunit epsilon [*Anoxybacillus vitaminiphilus*], 73%, gi|1408392372|WP_111644740.1
F0F1 ATP synthase subunit epsilon [*Bacillus* sp. J37], 73%, gi|651531384|WP_026563116.1
MULTISPECIES: F0F1 ATP synthase subunit epsilon [*Bacillus*], 73%, gi|736227472|WP_034318329.1
F0F1 ATP synthase subunit epsilon [*Bacillus xiamenensis*], 73%, gi|495630347|WP_008354926.1
F0F1 ATP synthase subunit epsilon [*Bacillus fastidiosus*], 72%, gi|1054351039|WP_066230885.1
F0F1 ATP synthase subunit epsilon [*Bacillus onubensis*], 71%, gi|1272187322|WP_099360911.1
MULTISPECIES: ATP synthase F0F1 subunit epsilon [*Bacillus*], 73%, gi|915975869|WP_050944437.1
F0F1 ATP synthase subunit epsilon [*Bacillus* sp. MBGLi79], 81%, gi|1339810892|AUZ40790.1
F0F1 ATP synthase subunit epsilon [*Bacillus pumilus*], 73%, gi|1002946034|WP_061409853.1
F0F1 ATP synthase subunit epsilon [*Bacillus* sp. YN-1], 71%, gi|1493450619|WP_121448499.1
ATP synthase epsilon chain [*Bacillus pumilus*], 73%, gi|763278706|WP_044140142.1
MULTISPECIES: F0F1 ATP synthase subunit epsilon [*Bacillus*], 72%, gi|736652987|WP_034660282.1
F0F1 ATP synthase subunit epsilon [*Bacillus onubensis*], 70%, gi|1272175367|WP_099354575.1
MULTISPECIES: F0F1 ATP synthase subunit epsilon [*Bacillus*], 72%, gi|495618814|WP_008343393.1
F0F1 ATP synthase subunit epsilon [*Bacillus safensis*], 72%, gi|1207611961|WP_087977756.1
MULTISPECIES: ATP synthase epsilon chain [*Bacillus*], 72%, gi|489307156|WP_003214592.1
F0F1 ATP synthase subunit epsilon [*Bacillus pumilus*], 72%, gi|1274554308|WP_099682181.1
F0F1 ATP synthase subunit epsilon [*Bacillus australimaris*], 72%, gi|983547050|WP_060698605.1
F0F1 ATP synthase subunit epsilon [*Bacillus indicus*], 71%, gi|657860862|WP_029566603.1
F0F1 ATP synthase subunit epsilon [*Bacillus alveayuensis*], 71%, gi|765542636|WP_044749357.1
F0F1 ATP synthase subunit epsilon [*Bacillus* sp. NMTD17], 72%, gi|1360795247|WP_106071342.1
MULTISPECIES: F0F1 ATP synthase subunit epsilon [*Anoxybacillus*], 67%, gi|765534407|WP_044741555.1
F0F1 ATP synthase subunit epsilon [*Bacillus stratosphericus*], 71%, gj|494762213|WP_107497623.1
F0F1 ATP synthase subunit epsilon [*Bacillus sinesaloumensis*], 70%, gi|1148930458|WP_077619903.1
F0F1 ATP synthase subunit epsilon [*Bacillus weihaiensis*], 71%, gi|1119658527|WP_072578188.1
F0F1 ATP synthase subunit epsilon [*Bacillus indicus*], 71%, gi|657040285|WP_029283365.1
F0F1 ATP synthase subunit epsilon [*Bacillus* sp. HNG], 69%, TABLE 2-continued gi|1452393681|WP_116352015.1
F0F1 ATP synthase subunit epsilon [*Bacillus* sp. HMSC76G11], 69%,
gi|1093537853|WP_070877088.1
MULTISPECIES: F0F1 ATP synthase subunit epsilon [*Bacillus*], 68%,
gi|736761603|WP_034765168.1
MULTISPECIES: F0F1 ATP synthase subunit epsilon [*Bacillus*], 68%,
gi|692164220|WP_032086917.1
F0F1 ATP synthase subunit epsilon [*Bacillus* sp. UMB0893], 69%,
gi|1325663800|WP_101567345.1
F0F1 ATP synthase subunit epsilon [*Bacillus* sp. MKU004], 68%,
gi|1035730730|WP_064567821.1
MULTISPECIES: F0F1 ATP synthase subunit epsilon [*Bacillus*], 68%,
gi|764371645|WP_044339984.1
F0F1 ATP synthase subunit epsilon [*Bacillus litoralis*], 71%,
gi|1054559304|WP_066328627.1
ATP synthase epsilon chain [*Bacillus pumilus*], 71%, gi|1129140162|OLP66784.1
F0F1 ATP synthase subunit epsilon [*Bacillus timonensis*], 69%,
gi|498363035|WP_010677191.1
F0F1 ATP synthase subunit epsilon [*Parageobacillus thermoglucosidasius*], 69%,
gi|1035712219|WP_064552783.1
MULTISPECIES: F0F1 ATP synthase subunit epsilon [*Geobacillus*], 69%,
gi|496156185|WP_008880692.1
F0F1 ATP synthase subunit epsilon [*Bacillus aquimaris*], 68%,
gi|1430927033|WP_113969229.1
F0F1 ATP synthase subunit epsilon [*Anoxybacillus tepidamans*], 67%,
gi|653159045|WP_027408017.1
ATP synthase epsilon chain [*Parageobacillus toebii*], 69%, gi|1004920835|KYD29843.1
MULTISPECIES: F0F1 ATP synthase subunit epsilon [Bacillaceae], 69%,
gi|1011859921|WP_062678125.1
F0F1 ATP synthase subunit epsilon [*Bacillus alkalitelluris*], 71%,
gi|1154169450|WP_078543435.1
F0F1 ATP synthase subunit epsilon [*Bacillus camelliae*], 70%,
gi|1316769867|WP_101356051.1
F0F1 ATP synthase subunit epsilon [*Geobacillus* genomosp. 3], 70%,
gi|530784737|WP_020961503.1
F0F1 ATP synthase subunit epsilon [*Bacillus* sp. SJS], 68%, gi|737427371|WP_035408062.1
F0F1 ATP synthase subunit epsilon [*Bacillus methanolicus*], 68%,
gi|489441322|WP_003346791.1
F0F1 ATP synthase subunit epsilon [*Bacillus horikoshii*], 68%,
gi|1025825400|WP_063559286.1
F0F1 ATP synthase subunit epsilon [*Bacillus salsus*], 69%, gi|1222808566|WP_090853330.1
F0F1 ATP synthase subunit epsilon [*Bacillus aquimaris*], 67%,
gi|1031446442|WP_064091927.1
F0F1 ATP synthase subunit epsilon [*Bacillus humi*], 67%, gi|953347474|WP_057998216.1
ATP synthase epsilon chain [*Geobacillus stearothermophilus*], 69%,
gi|1017231308|KZE96595.1
MULTISPECIES: F0F1 ATP synthase subunit epsilon [*Geobacillus*], 70%,
gi|1017204529|WP_063167198.1
F0F1 ATP synthase subunit epsilon [*Geobacillus lituanicus*], 70%,
gi|1229394455|WP_094239354.1
F0F1 ATP synthase subunit epsilon [*Geobacillus thermodenitrificans*], 69%,
gi|1293369325|WP_100660569.1
F0F1 ATP synthase subunit epsilon [*Bacillus bataviensis*], 67%,
gi|494146406|WP_007086152.1
F0F1 ATP synthase subunit epsilon [*Bacillus* sp. CHD6a], 68%,
gi|983512443|WP_060664609.1
F0F1 ATP synthase subunit epsilon [*Bacillus horikoshii*], 68%,
gi|1207658166|WP_088019729.1
F0F1 ATP synthase subunit epsilon [*Bacillus* sp. LL01], 68%,
gi|847255533|WP_047970236.1
F0F1 ATP synthase subunit epsilon [*Bacillus soli*], 68%, gi|1053820122|WP_066072952.1
F0F1 ATP synthase subunit epsilon [*Geobacillus* sp. 46C-IIa], 69%,
gi|1173351582|WP_081207861.1
F0F1 ATP synthase subunit epsilon [*Bacillus methanolicus*], 69%,
gi|489446343|WP_003351763.1
MULTISPECIES: F0F1 ATP synthase subunit epsilon [*Geobacillus*], 68%,
gi|765520579|WP_044732826.1
F0F1 ATP synthase subunit epsilon [*Bacillus* sp. FJAT-14578], 68%,
gi|654945804|WP_028395968.1
F0F1 ATP synthase subunit epsilon [*Parageobacillus thermantarcticus*], 68%,
gi|1222906556|WP_090949501.1
F0F1 ATP synthase subunit epsilon [*Bacillus marisflavi*], 68%,
gi|850295930|WP_048004873.1
F0F1 ATP synthase subunit epsilon [*Bacillus marisflavi*], 68%,
gi|850330602|WP_048014185.1

In one embodiment, an amino acid linker (X2) is present between X1 and X3, and an amino acid linker (X4) is present between X3 and X5. Any suitable amino acid linker may be used: extensive guidance is provided in the examples that follow. In various embodiments, X2 is an amino acid linker of between 0-2, 1-2, 0, 1, or 2 amino acids in length. In various further embodiments:

- X2 is an amino acid linker selected from the group consisting of A, S, P, V. T, TS, ID, or wherein X2 is absent;
- X2 is an amino acid linker selected from the group consisting of A, S, V, T, TS, and ID; or
- X2 is an amino acid linker selected from the group consisting of A. S. V. and T.

In other embodiments, X4 is an amino acid linker of between 1-5, 1-4, 1-3, 1-2, 1, 2, 3, 4, or 5 amino acids in length, or wherein X4 is absent. In various further embodiments:

- X4 is an amino acid linker selected from the group consisting of AT, A, SA, GA, FF, PPPP (SEQ ID NO: 20), FL, GTSG (SEQ ID NO: 21), P, S, ANEFM (SEQ ID NO: 22), or wherein X4 is absent;
- X4 is an amino acid linker selected from the group consisting of AT, A, SA, GA, FF, FL, P, and S; or
- X4 is an amino acid linker selected from the group consisting of A, FF, FL, and GTSG (SEQ ID NO: 21).

In further specific embodiments:

- X2 and X4 are both A;
- X2 is S and X4 is A;
- X2 is absent and X4 is FF;
- X2 is V and X4 is FL;
- X2 is T and X4 is GTSG (SEQ ID NO: 21); or
- X2 is S and X4 is SA.

In another embodiment, X2 and X4 do not include any proline residues, to maintain the linkers as flexible.

In further embodiments, the fusion protein comprises an amino acid sequence at least 90%, 91%, 92%, 93%, 94%95%, 96%, 97%, 98%, 99%, or 100% identical along the length of the amino acid sequence selected from the group consisting of SEQ ID NOS:7-11 (name referring to the designation used in the examples that follow), or that are the same as the sequences below but the linkers (X2 and X4) shown below (highlighted) are substituted with linkers for other constructs shown in Table 3 in the examples that follow:

SEQ ID NO: 7
GO-ATeam-A1
Fusion Protein including mKOk fluorescent protein (amino acids 1-218), a first alanine linker (amino acid 219), an ATP binding protein (amino acids 220-351), a second alanine linker (amino acid 352), and cpmEGFP fluorescent protein (amino acids 353-598)
(M)VSVIKPEMKMRYYMDGSVNGHEFTIEGEGTGRPYEGHQEMTLRVTMA
EGGPMPFAFDLVSHVFCYGHRVFTKYPEEIPDYFKQAFPEGLSWERSLEF
EDGGSASVSAHISLRGNTFYHKSKFTGVNFPADGPIMQNQSVDWEPSTEK
ITASDGVLKGDVTMYLKLEGGGNHKCQFKTTYKAAKEILEMPGDHYIGHR
LVRKTEGNITEQVEDAVAHS A
(M)KTVKVNITTPDGPVYDADIEMVSVRAESGDLGILPGHIPTKAPLKIG
AVRLKKDGQTEMVAVSGGTVEVRPDHVTINAQAAETAEGIDKERAEAARQ
RAQERLNSQSDDTDIRRAELALQRALNRLDVAGK ADGSVQLADHYQQNT
PIGDGPVLLPDNHYLSTQSKLSKDPNEKRDHMVLLEFVTAAGITLGMDEL
YKGGSGGMVSKGEELFTGVVPILVELDGDVNGHKFSVSGEGEGDATYGKL
TLKFICTTGKLPVPWPTLVTTLTYGVQCFSRYPDHMKQHDFEKSAMPEGY
VQERTIFFKDDGNYKTRAEVKFEGDTLVNRIELKGIDFKEDGNILGHKLE
YNYNSHNVYIMADKQKNGIKVNFKIRHNIEEA SEQ ID NO: 8
D5
(M)VSVIKPEMKMRYYMDGSVNGHEFTIEGEGTGRPYEGHQEMTLRVTMA
EGGPMPFAFDLVSHVFCYGHRVFTKYPEEIPDYFKQAFPEGLSWERSLEF
EDGGSASVSAHISLRGNTFYHKSKFTGVNFPADGPIMQNQSVDWEPSTEK
ITASDGVLKGDVTMYLKLEGGGNHKCQFKTTYKAAKEILEMPGDHYIGHR
LVRKTEGNITEQVEDAVAHS
S(M)KTVKVNITTPDGPVYDADIEMVSVRAESGDLGILPGHIPTKAPLKI
GAVRLKKDGQTEMVAVSGGTVEVRPDHVTINAQAAETAEGIDKERAEAAR
QRAQERLNSQSDDTDIRRAELALQRALNRLDVAGKA
DGSVQLADHYQQNTPIGDGPVLLPDNHYLSTQSKLSKDPNEKPDHMVLLE
FVTAAGITLGMDELYKGGSGGMVSKGEELFTGVVPILVELDGDVNGHKFS
VSGEGEGDATYGKLTLKFICTTGKLPVPWPTLVTTLTYGVQCFSRYPDHM
KQHDFFKSAMPEGYVQERTIFFKDDGNYKTRAEVKFEGDTLVNRIELKGI
DFKEDGNILGHKLEYNYNSHNVYIMADKQKNGIKVNFKIRHNIEEA SEQ ID NO: 9
F1
(M)VSVIKPEMKMRYYMDGSVNGHEFTIEGEGTGRPYEGHQEMTLRVTMA
EGGPMPFAFDLVSHVFCYGHRVFTKYPEEIPDYFKQAFPEGLSWERSLEF
EDGGSASVSAHISLRGNTFYHKSKFTGVNFPADGPIMQNQSVDWEPSTEK
ITASDGVLKGDVTMYLKLEGGGNHKCQFKTTYKAAKEILEMPGDHYIGHR
LVRKTEGNITEQVEDAVAHS (no linker)
(M)KTVKVNITTPDGPVYDADIEMVSVRAESGDLGILPGHIPTKAPLKIG
AVRLKKDGQTEMVAVSGGTVEVRPDHVTINAQAAETAEGIDKERAEAARQ
RAQERLNSQSDDTDIRRAELALQRALNRLDVAGKFF
DGSVQLADHYQQNTPIGDGPVLLPDNHYLSTQSKLSKDPNEKRDHMVLLE
FVTAAGITLGMDELYKGGSGGMVSKGEELFTGVVPILVELDGDVNGHKFS
VSGEGEGDATYGKLTLKFICTTGKLPVPWPTLVTTLTYGVQCFSRYPDHM
KQHDFFKSAMPEGYVQERTIFFKDDGNYKTRAEVKFEGDTLVNRIELKGI
DFKEDGNILGHKLEYNYNSHNVYIMADKQNGIKVNFKIRHNIEEA SEQ ID NO: 10
G1
(M)VSVIKPEMKMRYYMDGSVNGHEFTIEGEGTGRPYEGHQEMTLRVTMA
EGGPMPFAFDLVSHVFCYGHRVFTKYPEEIPDYFKQAFPEGLSWERSLEF
EDGGSASVSAHISLRGNTFYHKSKFTGVNFPADGPIMQNQSVDWEPSTEK
ITASDGVLKGDVTMYLKLEGGGNHKCQFKTTYKAAKEILEMPGDHYIGHR
LVRKTEGNITEQVEDAVAHS V
(M)KTVKVNITTPDGPVYDADIEMVSVRAESGDLGILPGHIPTKAPLKIG -continued

AVRLKKDGQTEMVAVSGGTVEVRPDHVTINAQAAETAEGIDKERAEAARQ

RAQERLNSQSDDTDIRRELALQRLNRLDVAGKFL

DGSVQLADHYQQNTPIGDGPVLLPDNHYLSTQSKLSKDPNEKRDHMVLLE

FVTAAGITLGMDELYKGGSGGMVSKGEELFTGVVPILVELDGDVNGHKFS

VSGEGEGDATYGKLTLKFICTTGKLPVPWPTLVTTLTYGVQCFSRYPDHM

KQHDFFKSAMPEGYVQERTIFFKDDGNYKTRAEVKFEGDTLVNRIELKGI

DFKEDGNILGHKLEYNYNSHNVYIMADKQKNGIKVNFKIRHNIEEA

SEQ ID NO: 11
G9
(M)VSVIKPEMKMRYYMDGSVNGHEFTIEGEGTGRPYEGHQEMTLRVTMA

EGGPMPFAFDLVSHVFCYGHRVFTKYPEEIPDYFKQAFPEGLSWERSLEF

EDGGSASVSAHISLRGNTFYHKSKFTGVNFPADGPIMQNQSVDWEPSTEK

ITASDGVLKGDVTMYLKLEGGGNHKCQFKTTYKAAKEILEMPGDHYIGHR

LVRKTEGNITEQVEDAVAHS *T*

(M)KTVKVNITTPDGPVYDADIEMVSVRAESGDLGILPGHIPTKAPLKIG

AVRLKKDGQTEMVAVSGGTVEVRPDHVTINAQAAETAEGIDKERAEAARQ

RAQERLNSQSDDTDIRRAEIALQRALNRLDVAGKGTSG

DGSVQLADHYQQNTPIGDGPVLLPDNHYLSTQSKLSKDPNEKRDHMVLLE

FVTAAGITLGMDELYKGGSGGMVSKGEELFTGVVPILVELDGDVNGHKFS

VSGEGEGDATYGKLTLKFICTTGKLPVPWPTLVTTLTYGVQCFSRYPDHM

KQHDFFKSAMPEGYVQERTIFFKDDGNYKTRAEVKFEGDTLVNRIELKGI

DFKEDGNILGHKLEYNYNSHNVYIMADKQKNGIKVNFKIRHNIEFA

In a second aspect, the disclosure provides control fusion proteins that can be used together with the active fusion proteins of the first aspect of the disclosure, for example, as a control in assays to detect and measure ATP in living cells. The control fusion proteins have the same general formula (X1-X2-X3-X4-X5) as the fusion proteins of the first aspect of the disclosure. All embodiments of the X1, X2, X4, and X5 domains disclosed for the first aspect are equally applicable in the control fusion proteins. The X3 domain differs in the control fusion proteins by comprising a control protein that does not bind to ATP. Any suitable control protein can be used. In one embodiment, the control protein comprises the amino acid sequence at least 65%, 67%, 68%, 70%, 75%, 80%, 85%, 90%, 91%, 92%, 93%, 94%, 95%, 96%, 97%, 98%, 99%, or 100% identical along the length of the amino acid sequence of SEQ ID NO: 12, wherein the underlined and bold font residues must be K:

SEQ ID NO: 12
(M)KTVKVNITTPDGPVYDADIEMVSVRAESGDLGILPGHIPTKAPLKIG

AVRLKKDGQTEMVAVSGGTVEVRPDHVTINAQAAETAEGIDKERAEAARQ

RAQERLNSQSDDTDIRRAELALQKALNKLDVAGK

The control proteins of this embodiment are closely related to the ATP binding proteins disclosed above, differing in having the required lysine residues noted above, which abolishes ATP binding activity.

In one specific embodiment, the control fusion proteins comprises an amino acid sequence at least 65%, 67%, 68%, 70%, 75%, 80%, 85%, 90%, 91%, 92%, 93%, 94% 95%, 96%, 97%, 98%, 99%, or 100% identical along the length of the amino acid sequence of SEQ ID NO:13, wherein the underlined and bold font residues must be K:

SEQ ID NO: 13
MVSVIKPEMKMRYYMDGSVNGHEFTIEGEGTGRPYEGHQEMTLRVTMAEG

GPMPFAFDLVSHVFCYGHRVFTKYPEEIPDYFKQAFPEGLSWERSLEFED

GGSASVSAHISLRGNTFYHKSKFTGVNFPADGPIMQNQSVDWEPSTEKIT

ASDGVLKGDVTMYLKLEGGGNHKCQFKTTYKAAKEILEMPGDHYIGHRLV

RKTEGNITEQVEDAVAHS *A*

MKTVKVNITTPDGPVYDADIEMVSVRAESGDLGILPGHIPTKAPLKIGAV

RLKKDGQTEMVAVSGGTVEVRPDHVTINAQAAETAEGIDKERAEAARQRA

QERLNSQSDDTDIRRAELALQKALNKLDVAGK *A*

DGSVQLADHYQQNTPIGDGPVLLPDNHYLSTQSKLSKDPNEKRDHMVLLE

FVTAAGITLGMDELYKGGSGGMVSKGEELFTGVVPILVELDGDVNGHKFS

VSGEGEGDATYGKLTLKFICTTGKLPVPWPTLVTTLTYGVQCFSRYPDHM

KQHDFFKSAMPEGYVQERTIFFKDDGNYKTRAEVKFEGDTLVNRIELKGI

DFKEDGNILGHKLEYNYNSHNVYIMADKQKNGIKVNFKIRHNIEEA

In this embodiment, the italicized and underlined linker residues can be modified to any suitable linker residues, including but not limited those listed in Table 3 of the examples.

As used throughout the present application, the term "protein" or is used in its broadest sense to refer to a sequence of subunit amino acids. The polypeptides described herein may be chemically synthesized or recombinantly expressed.

As will be understood by those of skill in the art, the fusion proteins of the disclosure may include additional residues at the N-terminus, C-terminus, or both that are not present in the described fusion proteins; these additional residues are not included in determining the percent identity of the polypeptides of the disclosure relative to the reference polypeptide. Such residues may be any residues suitable for an intended use, including but not limited to ligands suitable for purposes of purification (His tags, etc.), and additional peptide domains that add functionality to the polypeptides.

In one embodiment, changes relative to the reference fusion proteins comprises conservative amino acid substitution. As used herein, "conservative amino acid substitution" means amino acid or nucleic acid substitutions that do not alter or substantially alter fusion protein or domain function or other characteristics. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in the assays described herein to confirm that a desired activity is retained.

In another aspect, the disclosure provides polynucleotides encoding the fusion protein or control fusion protein of any embodiment or combination of embodiments of the disclosure. The polynucleotides may comprise RNA or DNA. Such polynucleotides may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what polynucleotides will encode the fusion proteins of the disclosure.

In another aspect, the disclosure provides recombinant expression vectors comprising the polynucleotides of any embodiment or combination of embodiments of the disclosure operatively linked to a promoter sequence capable of directing expression of the polynucleotide. "Recombinant expression vector" includes vectors that operatively link the polynucleotides to any promoter sequence capable of effecting expression of the fusion proteins. "Promoter sequences" operatively linked to the nucleic acid sequences of the disclosure are nucleic acid sequences capable of effecting the expression of the polynucleotides. The promoter need not be contiguous with the polynucleotide, so long as it functions to direct polynucleotide expression. Thus, for example, intervening untranslated yet transcribed sequences can be present between a promoter sequence and the polynucleotide and the promoter sequence can still be considered "operably linked" to the coding sequence. Such expression vectors can be of any type known in the art, including but not limited plasmid and viral-based expression vectors. The promoter may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). In various embodiments, the expression vector may comprise a plasmid, viral-based vector, or any other suitable expression vector.

In a further aspect, the present disclosure provides host cells that comprise the recombinant expression vectors disclosed herein, wherein the host cells can be either prokaryotic or eukaryotic. The cells can be transiently or stably engineered to incorporate the expression vector of the disclosure. A method of producing a fusion protein according to the disclosure is an additional part of the disclosure. The method comprises the steps of (a) culturing a host according to this aspect of the disclosure under conditions conducive to the expression of the fusion protein, and (b) optionally, recovering the expressed fusion protein. The expressed fusion protein can be recovered from the cell free extract or the cell culture medium.

In another aspect, the disclosure provides kits comprising:
(a) the fusion protein of any embodiment or combination of embodiments of the disclosure, the polynucleotide encoding the fusion protein, the expression vector comprising the polynucleotide encoding the fusion protein and/or the recombinant host cell comprising the expression vector comprising the polynucleotide encoding the fusion protein;
(b) the control fusion protein of any embodiment or combination of embodiments of the disclosure, the polynucleotide encoding the control fusion protein, the expression vector comprising the polynucleotide encoding the control fusion protein and/or the recombinant host cell comprising the expression vector comprising the polynucleotide encoding the control fusion protein.

The kits of this aspect may be used, for example, to detect and measure ATP in living cells, as detailed in the examples that follow.

ATP Binding Fusion Proteins

Polynucleotides encoding an ATP binding fusion protein are provided according to aspects of the present disclosure wherein the ATP binding fusion protein includes: a first fluorophore that is a FRET acceptor having an acceptor excitation wavelength and a FRET emission wavelength, the first fluorophore having an N-terminus and a C-terminus; an ATP binding protein having an N-terminus and a C-terminus; and a second fluorophore that is a FRET donor having a donor excitation wavelength and a donor emission wavelength, the second fluorophore having an N-terminus and a C-terminus, wherein a first linker is disposed between the C-terminus of the first fluorophore and the N-terminus of the ATP binding protein and a second linker is disposed between the C-terminus of the ATP binding protein and the N-terminus of the second fluorophore, and wherein the first fluorophore, ATP binding protein, and second fluorophore are operably linked such that binding of ATP by the ATP binding protein causes interaction of the first fluorophore and second fluorophore to produce a FRET emission signal when exposed to light having the donor excitation wavelength.

According to aspects of the present disclosure, the first linker of the ATP binding fusion protein is an alanine residue and the second linker is an alanine residue.

According to aspects of the present disclosure, the first linker of the ATP binding fusion protein a serine residue and the second linker is an alanine residue.

According to aspects of the present disclosure, the first linker of the ATP binding fusion protein is a nullity and the second linker is a phenylalanine-phenylalanine dipeptide residue.

According to aspects of the present disclosure, the first linker of the ATP binding fusion protein is a valine residue and the second linker is a phenylalanine-leucine dipeptide residue.

According to aspects of the present disclosure, the first linker of the ATP binding fusion protein is a threonine residue and the second linker is a glycine-threonine-srine-glycine peptide residue.

According to aspects of the present disclosure, the first linker of the ATP binding fusion protein is a serine residue and the second linker is a serine-alanine dipeptide residue.

According to aspects of the present disclosure, the second linker of the ATP binding fusion protein is not and/or does not include an asparagine residue.

Fusion proteins are provided according to aspects of the present disclosure wherein the fusion protein includes: a first fluorophore that is a FRET acceptor having an acceptor excitation wavelength and a FRET emission wavelength, the first fluorophore having an N-terminus and a C-terminus; an ATP binding protein having an N-terminus and a C-terminus; and a second fluorophore that is a FRET donor having a donor excitation wavelength and a donor emission wavelength, the second fluorophore having an N-terminus and a C-terminus, wherein a first linker is disposed between the C-terminus of the first fluorophore and the N-terminus of the ATP binding protein and a second linker is disposed between the C-terminus of the ATP binding protein and the N-terminus of the second fluorophore, and wherein the first fluorophore, ATP binding protein, and second fluorophore are operably linked such that binding of ATP by the ATP binding protein causes interaction of the first fluorophore and second fluorophore to produce a FRET emission signal when exposed to light having the donor excitation wavelength.

According to aspects of the present disclosure, an ATP binding protein included a fusion protein is the ATP binding protein of SEQ ID NO: 5, encoded by SEQ ID NO: 14.

According to aspects of the present disclosure, an ATP binding protein included a fusion protein is a variant of SEQ ID NO: 5 which binds ATP and has 1, 2, 3, 4, 5, 6, 7, 8, 9, or 10 substitution mutations, additions or deletions compared to SEQ ID NO:5.

According to aspects of the present disclosure, an ATP binding protein included a fusion protein is a variant of SEQ ID NO: 5 which binds ATP and is encoded by a variant of SEQ ID NO: 14 which binds to SEQ ID NO:14 under high stringency hybridization conditions.

Control Fusion Proteins

Polynucleotides encoding a control fusion protein are provided according to aspects of the present disclosure wherein the control fusion protein includes: a first fluorophore that is a FRET acceptor having an acceptor excitation wavelength and an acceptor emission wavelength, the first fluorophore having an N-terminus and a C-terminus; a control mutant ATP binding protein having an N-terminus and a C-terminus, the control mutant ATP binding protein mutated such that it does not bind ATP; and a second fluorophore that is a FRET donor having a donor excitation wavelength and a donor emission wavelength, the second fluorophore having an N-terminus and a C-terminus, wherein a first linker is disposed between the C-terminus of the first fluorophore and the N-terminus of the control mutant ATP binding protein and a second linker is disposed between the C-terminus of the control mutant ATP binding protein and the N-terminus of the second fluorophore, and wherein the first fluorophore, control mutant ATP binding protein, and second fluorophore are operably linked to function as a control since the control mutant ATP binding protein does not bind ATP such that interaction of the first fluorophore and second fluorophore to produce a FRET emission signal when exposed to light having the donor excitation wavelength represents a non-specific background signal unrelated to presence of ATP.

According to aspects of the present disclosure, the first linker of the control fusion protein is an alanine residue and the second linker is an alanine residue.

According to aspects of the present disclosure, the first linker of the control fusion protein is a serine residue and the second linker is an alanine residue.

According to aspects of the present disclosure, the first linker of the control fusion protein is a nullity and the second linker is a phenylalanine-phenylalanine dipeptide residue.

According to aspects of the present disclosure, the first linker of the control fusion protein is a valine residue and the second linker is a phenylalanine-leucine dipeptide residue.

According to aspects of the present disclosure, the first linker of the control fusion protein is a threonine residue and the second linker is a glycine-threonine-serine-glycine peptide residue.

According to aspects of the present disclosure, the first linker of the control fusion protein is a serine residue and the second linker is a serine-alanine dipeptide residue.

According to aspects of the present disclosure, the second linker of the control fusion protein is not and/or does not include an asparagine residue.

A control fusion protein, the control fusion protein including: a first fluorophore that is a FRET acceptor having an acceptor excitation wavelength and a FRET emission wavelength, the first fluorophore having an N-terminus and a C-terminus; a control mutant ATP binding protein having an N-terminus and a C-terminus; and a second fluorophore that is a FRET donor having a donor excitation wavelength and a donor emission wavelength, the second fluorophore having an N-terminus and a C-terminus, wherein a first linker is disposed between the C-terminus of the first fluorophore and the N-terminus of the control mutant ATP binding protein and a second linker is disposed between the C-terminus of the control mutant ATP binding protein and the N-terminus of the second fluorophore, and wherein the first fluorophore, control mutant ATP binding protein, and second fluorophore are operably linked to function as a control since the control mutant ATP binding protein does not bind ATP such that interaction of the first fluorophore and second fluorophore to produce a FRET emission signal when exposed to light having the donor excitation wavelength represents a non-specific background signal unrelated to presence of ATP.

According to aspects of the present disclosure, an ATP binding protein included a control fusion protein is the ATP binding protein of SEQ ID NO: 15, encoded by SEQ ID NO: 16.

According to aspects of the present disclosure, a control mutant ATP binding protein which does not bind ATP included a control fusion protein is a variant of SEQ ID NO: 15 which does not bind ATP and has 1, 2, 3, 4, 5, 6, 7, 8, 9, or 10 substitution mutations, additions or deletions compared to SEQ ID NO: 15.

According to aspects of the present disclosure, a control mutant ATP binding protein included a fusion protein is a variant of SEQ ID NO: 15 which does not bind ATP and is encoded by a variant of SEQ ID NO: 16 which binds to SEQ ID NO: 16 under high stringency hybridization conditions.

According to aspects of the present disclosure, a polynucleotide described herein includes an operably linked promoter. According to aspects of the present disclosure, a polynucleotide described herein is included in an expression vector. According to aspects of the present disclosure, a polynucleotide and/or expression vector described herein is present in a host cell, such as, but not limited to, a stable transformant cell line expressing the polynucleotide and its encoded fusion protein.

According to aspects of the present disclosure, the donor fluorophore is cpmEGFP. According to aspects of the present disclosure, the acceptor fluorophore is mKOk.

It should be appreciated that while embodiments of the disclosure are described herein wherein the FRET donor fluorophore is positioned at the C-terminus of the ATP binding protein or the control mutant binding protein (with a linker disposed between the C-terminus of the ATP binding protein, or the control mutant binding protein, and the FRET donor fluorophore) and the FRET acceptor fluorophore is positioned at the N-terminus of the ATP binding protein or the control mutant binding protein (with a linker disposed between the N-terminus of the ATP binding protein, or the control mutant binding protein, and the FRET acceptor fluorophore), the relative positions of the fluorophores is optionally switched such that fusion proteins described herein have the FRET donor fluorophore positioned at the N-terminus of the ATP binding protein or the control mutant binding protein (with a linker disposed between the N-terminus of the ATP binding protein, or the control mutant binding protein, and the FRET donor fluorophore) and the FRET acceptor fluorophore is positioned at the C-terminus of the ATP binding protein, or the control mutant binding protein, (with a linker disposed between the C-terminus of the ATP binding protein, or the control mutant binding protein, and the FRET acceptor fluorophore).

Fluorophores

Examples of FRET donor/acceptor pairs generally include, but are not limited to, cyan fluorescent protein/yellow fluorescent protein (CFP-YFP) FRET pairs, green fluorescent protein/red fluorescent protein (GFP-RFP) FRET pairs, and other combinations.

In another aspect, the disclosure provides methods for determining a level of ATP in a cell of interest using the fusion proteins disclosed herein. The fusion proteins detect ATP in that binding of ATP by the ATP binding protein in the fusion protein causes interaction of the FRET acceptor polypeptide and the FRET donor polypeptide, resulting in emission of light that can be detected. Detection of emitted light can be carried out via any suitable assay or imaging format. In one embodiment, such methods comprise (a) expressing the fusion protein of any embodiment or combination of embodiments disclosed herein in one or more first cells, and generating one or more images selected from the group consisting of:
 (i) a first fluorescence image generated by detecting fluorescent signals produced by light having the FRET acceptor polypeptide emission wavelength emitted from the one or more first cells upon exposing the one or more first cells to light having the FRET donor polypeptide excitation wavelength; and/or
 (ii) a second fluorescence image generated by detecting fluorescent signals produced by light having the FRET acceptor polypeptide emission wavelength emitted from the one or more first cells upon exposing the one or more first cells to light having the FRET acceptor polypeptide excitation wavelength; and/or
 (iii) a third fluorescence image generated by detecting fluorescent signals produced by light having the FRET donor polypeptide emission wavelength emitted from the one or more first cells upon exposing the one or more first cells to light having the FRET donor polypeptide excitation wavelength; and
(b) determining a FRET ratio in the one or more first cells by comparing the output of fluorescent signals in the first fluorescent image, the second fluorescent image, and/or the third fluorescent image;
 wherein the level of ATP in the one or more first cells is proportional to the determined FRET ratio.

In this embodiment, "comparing" the output of fluorescent signals means dividing the output of fluorescent signals in one image by the output of fluorescent signals in a different image. For example:
 the output of fluorescent signals in the first fluorescent image can be divided by the output of fluorescent signals in the second fluorescent image;
 the output of fluorescent signals in the first fluorescent image can be divided by the output of fluorescent signals in the third fluorescent image;
 the output of fluorescent signals in the second fluorescent image can be divided by the output of fluorescent signals in the first fluorescent image;
 the output of fluorescent signals in the second fluorescent image can be divided by the output of fluorescent signals in the third fluorescent image;
 the output of fluorescent signals in the third fluorescent image can be divided by the output of fluorescent signals in the first fluorescent image; or
 the output of fluorescent signals in the third fluorescent image can be divided by the output of fluorescent signals in the second fluorescent image.

The "outputs" of fluorescent signals can be determined on any suitable basis, including but not limited to on a whole image basis, per cell basis, on a per pixel basis, or using any alternative intensity measurements.

In another embodiment, the methods further comprise expressing the control fusion protein of any embodiment or combination of embodiments of the disclosure in one or more first cells, and detecting a control signal produced by light having the acceptor emission wavelength emitted from the one or more first cells. Any suitable method for using the control signal to correct the determined FRET ratio may be used. In one embodiment, detecting the control signal comprises (c) expressing the control fusion protein of any embodiment or combination of embodiments disclosed herein in one or more control cells (such as the first cells, or second cells), and generating one or more images selected from the group consisting of:
 (i) a fourth fluorescence image generated by detecting fluorescent signals produced by light having the FRET acceptor polypeptide emission wavelength emitted from the one or more control cells upon exposing the one or more control cells to light having the FRET donor polypeptide excitation wavelength; and/or
 (ii) a fifth fluorescence image generated by detecting fluorescent signals produced by light having the FRET acceptor polypeptide emission wavelength emitted from the one or more control cells upon exposing the one or more control cells to light having the FRET acceptor polypeptide excitation wavelength; and/or
 (iii) a sixth fluorescence image generated by detecting fluorescent signals produced by light having the FRET donor polypeptide emission wavelength emitted from the one or more control cells upon exposing the one or more control cells to light having the FRET donor polypeptide excitation wavelength; and
(d) determining a control fusion FRET ratio in the one or more control cells by comparing the output of fluorescent signals in the fourth fluorescent image, the fifth fluorescent image, and/or the sixth fluorescent image;
 wherein alterations in the control fusion FRET ratio are determined to be the result of experimental conditions unrelated to ATP binding, and wherein the determined FRET ratio is corrected based on the alterations in the control fusion FRET ratio.

The one or more cells may be any cell or cell population in which determining ATP levels is of interest. In one embodiment, the one or more first cells are in culture in an incubator. In another embodiment, all imaging steps are performed without removing the one or more first cells from the incubator. In this embodiment, the cells are cultured in a suitable cell culture medium in an incubator, and the incubator is configured such that the cells to be assayed do not have to be removed from the incubator during observation and/or recording of assays for detecting ATP, such as changes in ATP due to contacting the cells with a test substance.

The assays can be used, for example, to test the effect of one or more test compounds on ATP levels in cells of interest. Thus, in one embodiment, the methods further comprise contacting the one or more first cells with one or more test substance and determining an effect of the test substance on the presence of ATP in the one or more first cells. The effect of the one or more test substance on the presence of ATP in the one or more first cells may be determined over any time period of interest, including but not limited to continuously or intermittently over a time period in the range of 1 minute to three months.

The IncuCyte® S3 Live Cell Analysis for Metabolism System for Live Cell Analysis of Intracellular ATP The IncuCyte® S3 hardware may be used for any method of the disclosure, and is composed of 2 components: 1) gantry and 2) controller. The gantry houses the microscope, camera, and consumable trays that enable automated image acquisition of live-cell cultures and is installed inside a standard tissue culture incubator. In the ATP application the microscope system contains a filter module that is tailored to collecting fluorescent images in the desired spectrum (or spectra). The controller contains processors, memory and data storage drives that enable image storage, data handling, database storage, file systems, automated image processing, graphing and over-the-network interaction from the client computer through a graphical user interface (GUI). The software on the controller serves 2 purposes: 1) server interaction, and 2) instrument control.

The gantry is installed in an incubator and houses the microscope and camera. The controller controls the microscope system and functions as a server. The controller plugs into a communications port, such as, but not limited to, an ethernet port. A graphical user interface (GUI) is loaded on to a computer and interacts with the controller (i.e. server) to control the microscope system and interact with the data. All automated image processing is completed on the controller according to aspects of the present disclosure.

Automated Image Capture

The Incucyte® S3 microscope moves to user defined locations of cell culture vessels, such as, but not limited to, 96-well plates, turns on the appropriate LED and captures images at a desired exposure time using a desired microscope objective, such as, 700 ms using the 10× objective.

The following data are derived from imaging of the objects, e.g. cells, ATP presence and/or level, and/or one or more additional metrics alone or in combination, are calculated for each object, each well, or each set of wells, stored in a database, and displayed to the user shortly following data acquisition in the client computer through the graphical user interface.

Typically wells are scanned every 2 hours, although more or less frequent scanning is an option. Following each scan, metrics are calculated and stored, for instance in the database, at those time points. For example, over the course of a 3 day experiment, 36 time points are collected for each metric, are concatenated into a time series and can be graphed over the course of the full experimental time frame, i.e. minutes, hours, days, weeks, months.

As described herein systems and methods of the present disclosure allow users to monitor the changes in ATP presence and/or levels over long periods of time in an automated, moderate throughput way. By contrast, previous methods are: 1) end point methods (can only get one or limited read(s) of the various measured parameters), 2) extremely disruptive methods, 3) require a user to move cells out of the incubator for analysis/visualization, 4) dependent on cell number, 5) indirect measurements of ATP production, and/or 6) low throughput (one well at a time, manual).

Embodiments of the compositions and methods of the disclosure are illustrated in the following examples. These examples are provided for illustrative purposes and are not considered limitations on the scope of the claimed compositions and methods.

Example 1

Linker Screening

A library with a diversity of approximately 14,000 unique mutants was screened for optimization of linker regions. Briefly, the screening was completed in bacterial cells where the specific mutant was expressed. Over 15000 individual colonies were evaluated for their brightness and FRET ratio using optical methods. Of these more than 15,000 colonies 400 were selected for further evaluation using protein lysates such that measurements could be made in both the ATP bound and unbound states. 12 potential colonies were selected for genetic sequencing, and cloned into mammalian expression vectors, and used for transient transfection experiments. Cells expressing these constructs were treated with the drugs that are known to reduce the amount of intracellular ATP. The signal window was calculated by subtracting the FRET ratio of the drug-treated cells from the FRET ratio of the vehicle-treated cells 2 h post treatment. The results are shown in FIG. 1. Error bars are SEM, n=3. The two-tailed P value for A1 and GO-ATeam1 equals 0.0084 (unpaired t test).

The linker sequences tested are shown in TABLE 3 below:

TABLE 3

| Mutant name | $1^{st}$ linker (N-terminus of the ATP-binding domain) | $2^{nd}$ linker (C-terminus of the ATP-binding domain) |
| --- | --- | --- |
| B7 | no linker between mKOk and the ATP-binding domain | AT |
| A1 (GO-ATeam-A1) SEQ ID NO: 1 | A | A |
| F7 | S | SA |
| D5 | S | A |
| G7 | no linker between mKOk and the ATP-binding domain | GA |
| F1 | no linker between mKOk and the ATP-binding domain | FF |

TABLE 3-continued

| Mutant name | 1st linker (N-terminus of the ATP-binding domain) | 2nd linker (C-terminus of the ATP-binding domain) |
|---|---|---|
| C5 | P | PPPP (SEQ ID NO: 20) |
| G1 | V | FL |
| G9 | T | GTSG (SEQ ID NO: 21) |
| C2 | no linker between mKOk and the ATP-binding domain | P |
| A10 | no linker between mKOk and the ATP-binding domain | no linker between the ATP-binding domain and cpmEGFP |
| E7 | TS | S |
| GO-ATeam1 | ID | ANEFM (SEQ ID NO: 22) |

Figure 2:
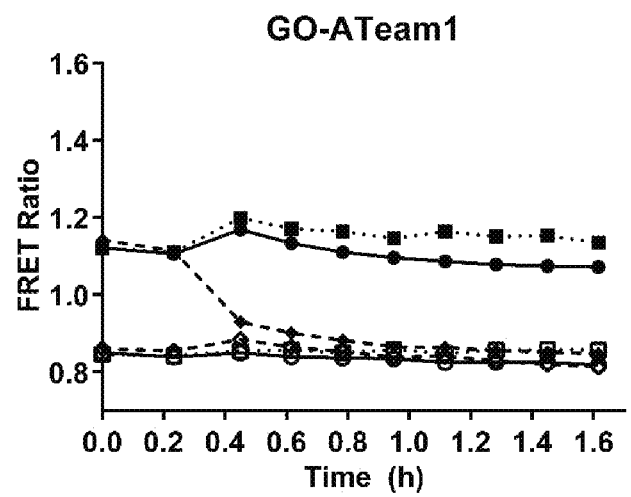
FIG. 2A-B are graphical comparisons of FRET ratios observed using exemplary fusion proteins of the disclosure ((A) GO-ATeam1; and (B) A1) in cell lines with stable expression of each sensor.
Figure 2:
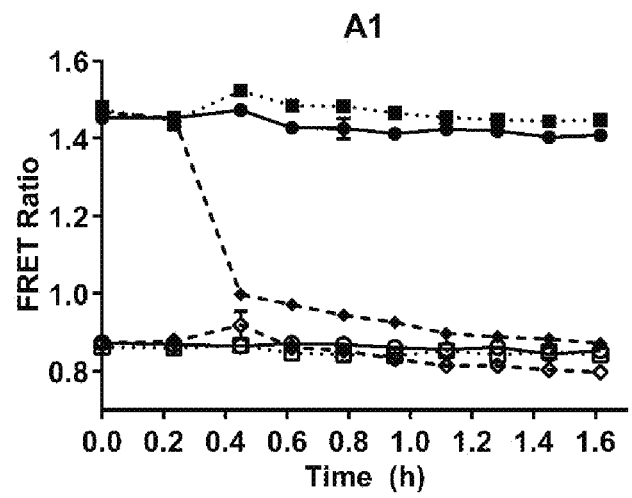

Cell lines were generated expressing construct A1 and Go-ATeam1 stably. i.e. the cells were infected via lentiviral transduction and selected using an antibiotic selection marker to generate stable lines. Cells were treated with 2.5 µM staurosporine to increase ATP and combined 40 mM 2-deoxy-D-Glucose (2-DG) and 4 mM potassium cyanide (KCN) to deplete ATP. The signal window in cells expressing sensor A1 was approximately twice that of the signal window in Go-ATeam1-expressing cell lines (FIG. 2A-B).

Figure 3A:
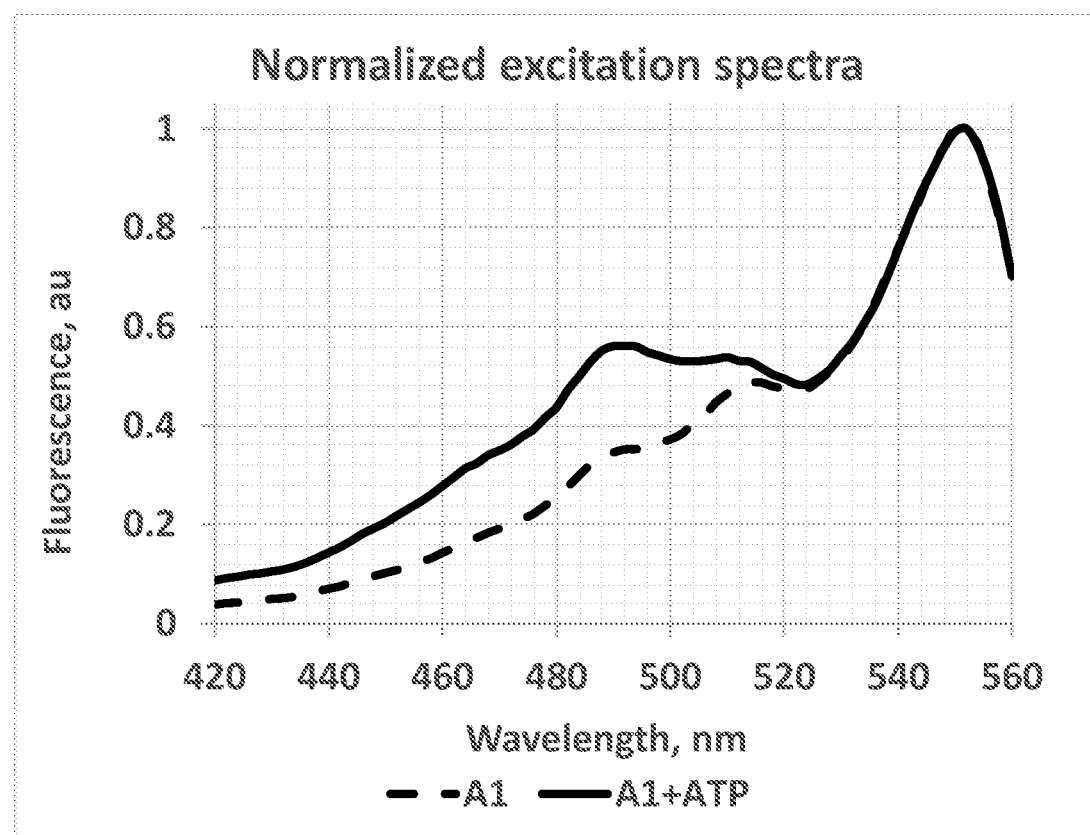
FIG. 3A-B are graphical comparisons of excitation spectra observed using exemplary fusion proteins of the disclosure incubated with and without 10 mM ATP. The performance of sensor A1 (GO-ATeam-A1) (FIG. 3A) illustrates a greater than 2-fold increase in signal window (comparing ATP bound (solid line) to ATP unbound state (dashed line)) when compared to the performance of the GO-Ateam1 sensor (FIG. 3B).
Figure 3B:
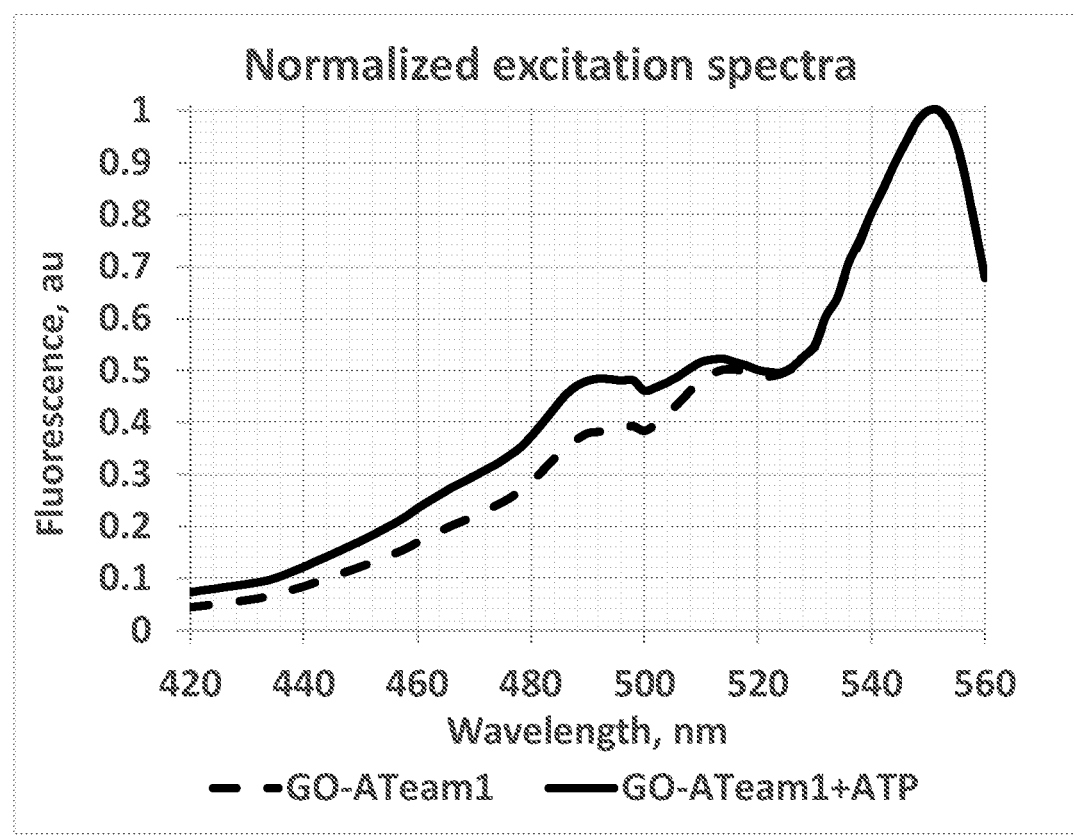

Purified proteins were incubated with and without 10 mM ATP and their excitation spectra were collected, FIGS. 3A and 3B. The difference between the spectra of ATP-treated and non-treated protein indicates the signal window. The performance of sensor A1 (GO-ATeam-A1) (FIG. 3A) illustrates a greater than 2-fold increase in signal window (comparing ATP bound (solid line) to ATP unbound state (dashed line)) when compared to the performance of the GO-ATeam1 sensor (FIG. 3B).

Example 2

A live cell imaging approach to categorize test substances as nontoxic, cytotoxic, or mitotoxic using the glucose/galactose switch model was evaluated using methods and compositions according to aspects of the present disclosure which assay ATP in living cells.

Substituting galactose for glucose in growth media blocks the ability of cells to generate ATP via glycolysis, conferring reliance on mitochondrial oxidative phosphorylation to generate ATP and enhancing sensitivity to mitochondrial-driven toxicity (L. D. Marroquin et al., *Toxicol Sci* 97(2), 539-547 (2007)). Cellular ATP levels were measured up to 24 hours following test substance treatment. Nontoxic test substances resulted in little to no change in ATP, cytotoxic test substances conferred a decrease in ATP in both glucose and galactose conditions, and mitotoxic test substances displayed leftward shift in potency under galactose conditions. Reductions in ATP could be observed in minutes, and transient reductions followed by recovery highlight the sensitivity and value of kinetic data using a live cell imaging approach using compositions and methods according to aspects of the present disclosure as described in further detail below.

Generation of ATP Sensor-Expressing Cell Lines

Cell lines stably expressing cytoATP (ATP-binding) and Control (mutated ATP-binding domain) sensors were generated by lentiviral transduction. A 3rd generation lentiviral system containing a bicistronic expression cassette was used to express the sensors. Specifically, the EF-1 alpha promoter was used to drive expression of the sensor and the puromycin selection marker using an intervening IRES sequence. Cells were seeded at 50,000 cells/well in 6-well plates the day prior to lentiviral infection. Cells were exposed to cytoATP or Control lentivirus in the presence of 8 µg/mL polybrene. After 24 h, media was replaced with polybrene-free media. Cells were passaged once, then subjected to puromycin selection to generate a stable, homogenous population of cells expressing cytoATP or Control sensors.

Cell Culture

Cells were purchased from ATCC+ (CRL-1658™) and maintained in a humidified 5% $CO_2$ atmosphere at 37° C. Cells were cultured in DMEM without glucose (Gibco) supplemented with 25 mM glucose, 1 mM sodium pyruvate, 5 mM HEPES, 10% FBS, 1% GlutaMax, and 1% Pen/Strep. Galactose media was prepared as described above except glucose was replaced by 10 mM galactose. For galactose adaptation, cells were split into glucose-containing DMEM, switched to galactose media on the second day after passage, then passaged twice more in galactose media before experimentation began.

ATP Assay

Measurement of ATP was performed by an IncuCyte® S3 equipped with a specialized FRET-based filter set and data acquisition module. The cytoATP sensor is a genetically-encoded indicator comprised of a FRET donor (cpmEGFP) and FRET acceptor (mKOk) connected by an ATP-binding domain. An increase in FRET is induced upon ATP binding. The Control sensor contains a mutated ATP binding domain and is used to provide a zero point for normalization and to monitor and correct for any artifacts affecting FRET signal readout. Sensor measurements were performed using dual-excitation ratio imaging. In a specific example, fluorescence emission of the acceptor fluorophore mKOk (567-589 nm) is collected following excitation of the donor fluorophore cpmEGFP (475495 nm, measurement of FRET) or direct excitation of the acceptor fluorophore mKOk (524-546 nm, measurement of total protein). A cellular analysis mask is generated by thresholding of the fluorescence images collected from direct mKOk excitation. This mask is also applied to complementary images collected in the FRET channel. Relative ATP level is reported as the cpmEGFP/mKOk excitation ratio, calculated by dividing the total integrated intensity measured from images collected with cpmEGFP excitation by that measured from images collected with mKOk excitation.

To generate concentration-response curves, data was corrected for each treatment and normalized to vehicle controls at a given time point using the following equation:

$$\frac{\left(\frac{Treatment_{cytoATP}}{\text{Average } Treatment_{Non-binding\ Control}}\right) - 1}{\left(\frac{Vehicle_{cytoATP}}{\text{Average } Vehicle_{Non-binding\ Control}}\right) - 1}$$

Figure 4A:
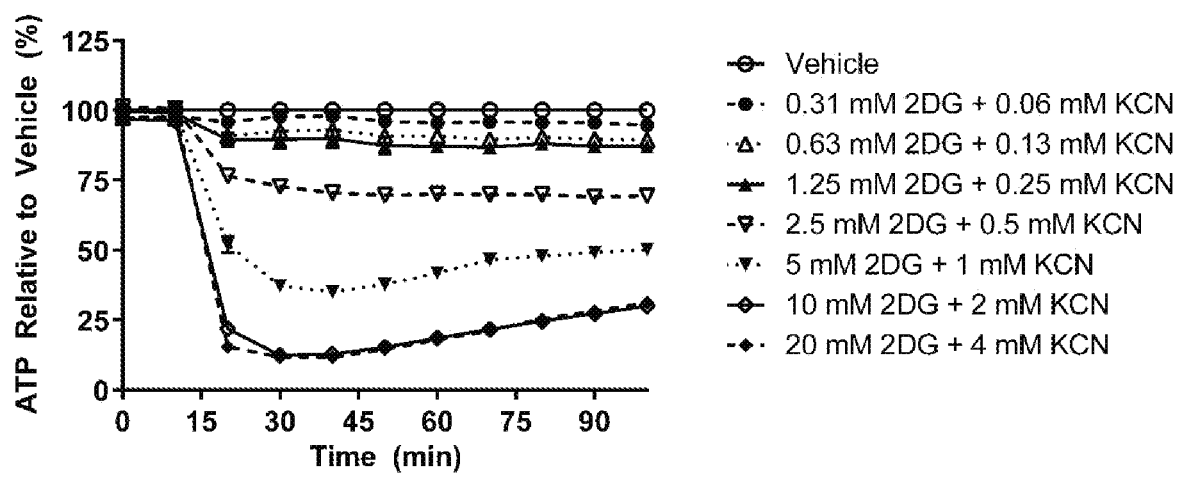
FIG. 4. ATP depletion via concurrent inhibition of glycolysis and OXPHOS by 2DG and KCN, respectively, on cells grown in standard media (FIG. 4A). Data demonstrate the time course of ATP depletion and concentration dependence of concurrent 2DG and KCN treatment. Comparison of cytotoxic (chlorpromazine, FIG. 4B) and mitotoxic (rotenone, FIG. 4C) compounds on cells grown in glucose or galactose media. The first two panels depict the effect of each compound over a 24 h time course in cells grown in glucose or galactose as indicated. The third panel depicts the concentration-response curve of each compound at the 24 h time point. Cytotoxic compounds show a similar effect under both media conditions, while mitotoxic compounds induce greater ATP depletion in cells grown in galactose.
Figure 4B:
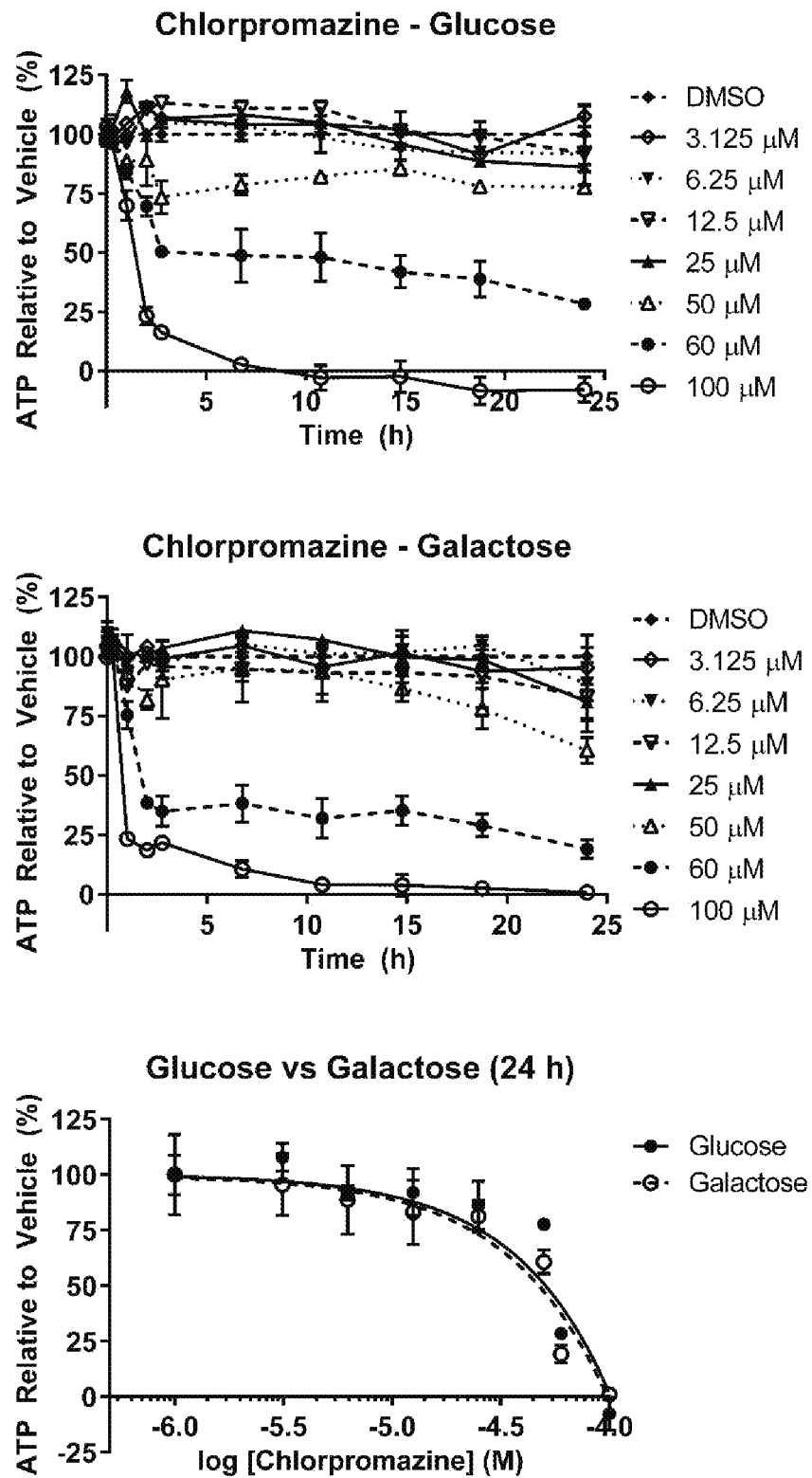
Figure 4C:
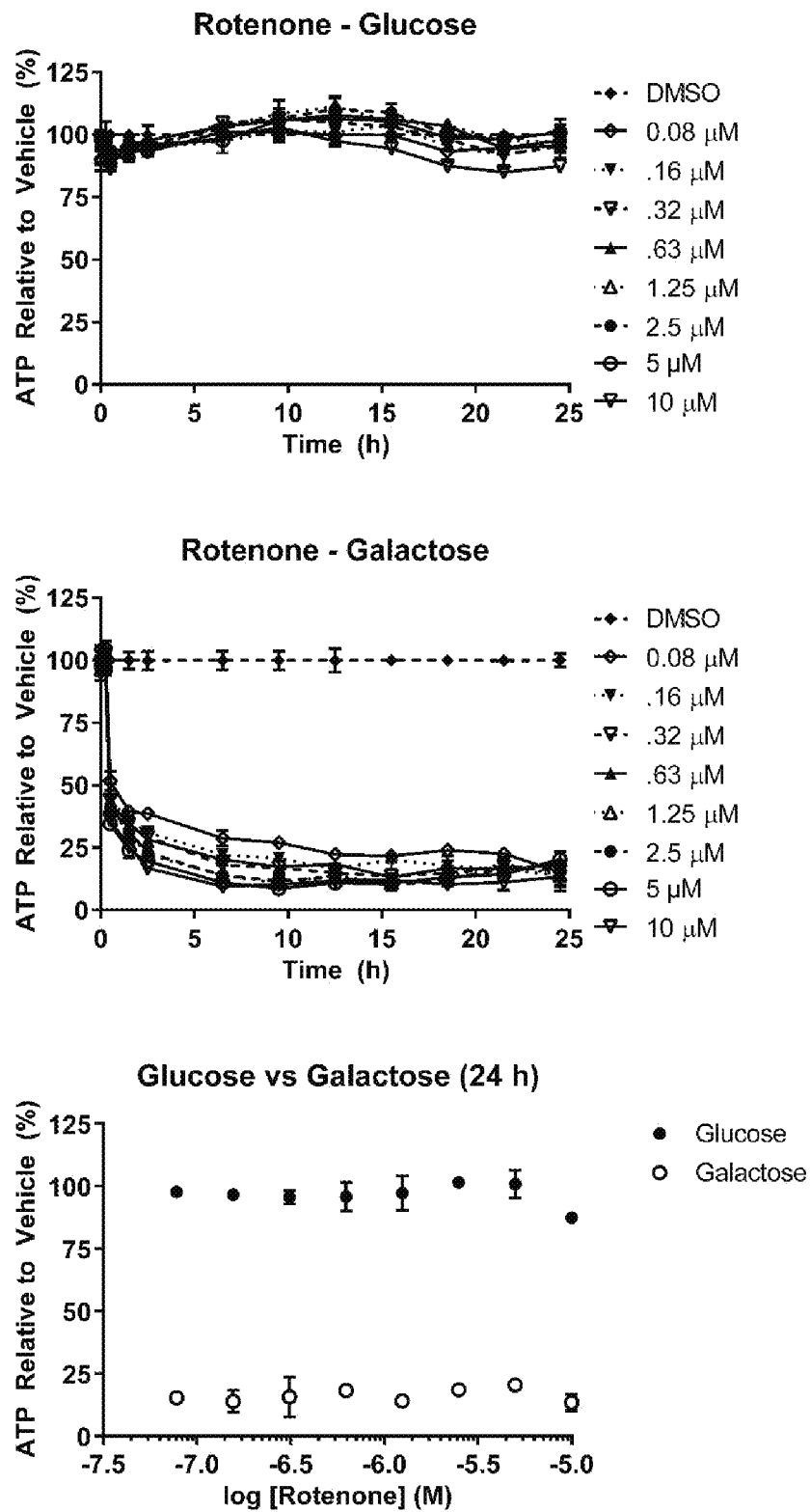

FIG. 4A: ATP depletion via concurrent inhibition of glycolysis and OXPHOS by 2DG and KCN, respectively, on cells grown in standard media. Data demonstrate the time course of ATP depletion and concentration dependence of concurrent 2DG and KCN treatment. FIGS. 4B and 4C show a comparison of cytotoxic (chlorpromazine, FIG. 4B) and mitotoxic (rotenone, FIG. 4C) compounds on cells grown in glucose or galactose media. The first two panels depict the effect of each compound over a 24 h time course in cells grown in glucose or galactose as indicated. The third panel depicts the concentration-response curve of each compound at the 24 h time point. Cytotoxic compounds show a similar effect under both media conditions, while mitotoxic compounds induce greater ATP depletion in cells grown in galactose.

Example 3

Materials and Methods

Cancer cell lines stably expressing a genetically encoded, fluorescent ATP sensor or a control (non-ATP binding) sensor were generated. Cell lines were cultured in recommended media conditions except for studies evaluating the effects of the glutaminase-1 (GLS1) inhibitor CB-839, for which cells were adapted to RPMI supplemented with 10% FBS prior to experimentation. ATP levels were monitored and analyzed using an IncuCyte® S3 equipped with a specialized filter set and data acquisition module. Cellular ATP levels were measured over the course of hours to days following compound treatment.

Data Summary

Figure 5A:
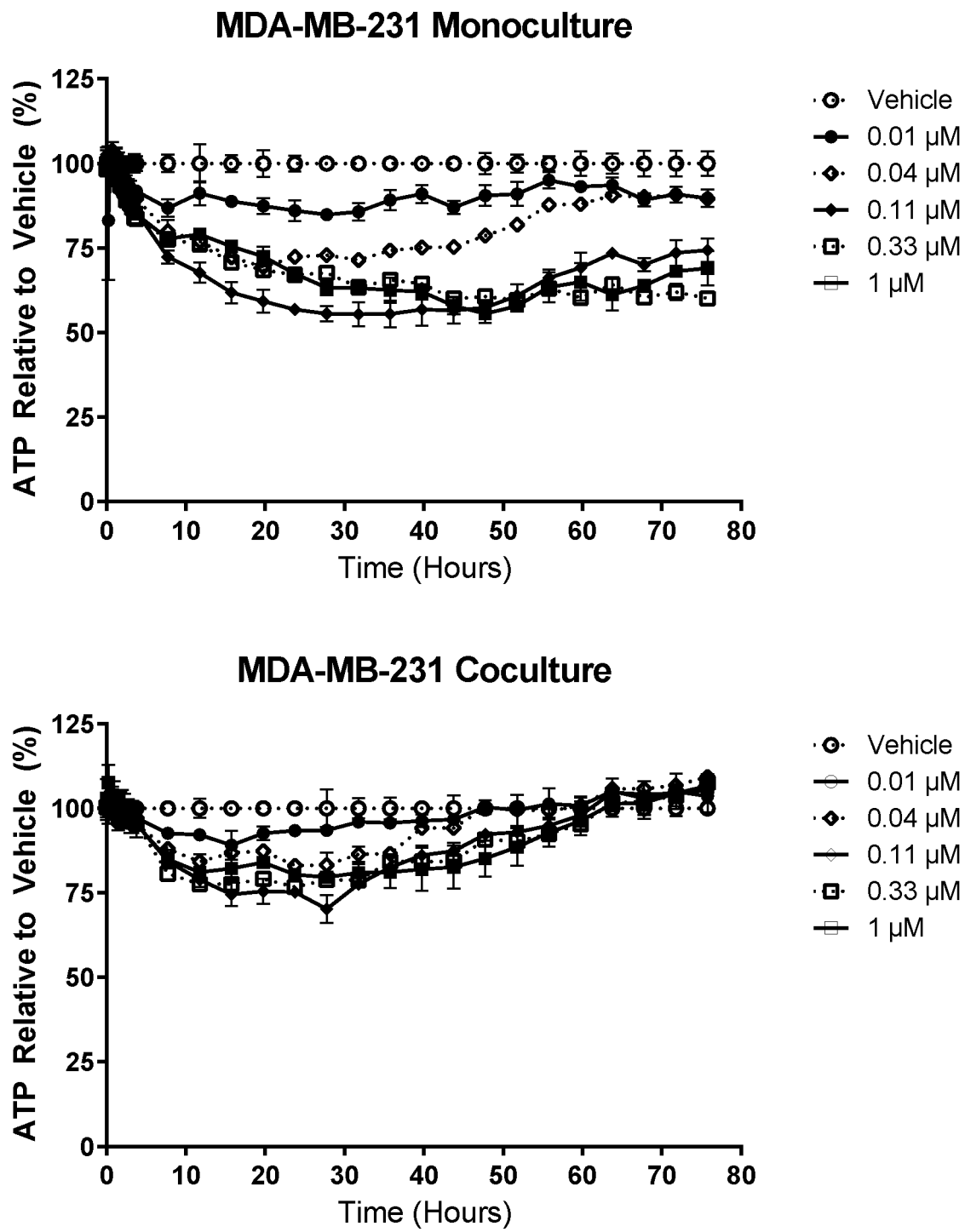
FIG. 5A-B. Effect of CB-839 in breast cancer cell lines in mono- or co-culture with fibroblasts. Representative data demonstrate prolonged ATP depletion in triple negative breast cancer (TNBC) cells, which is attenuated by co-culture with CCD-1068Sk fibroblasts (FIG. 5A). In contrast, receptor positive cells demonstrated recovery from CB-839 treatment within 48 h, and the response was unaffected by the presence of fibroblasts (FIG. 5B).
Figure 5B:
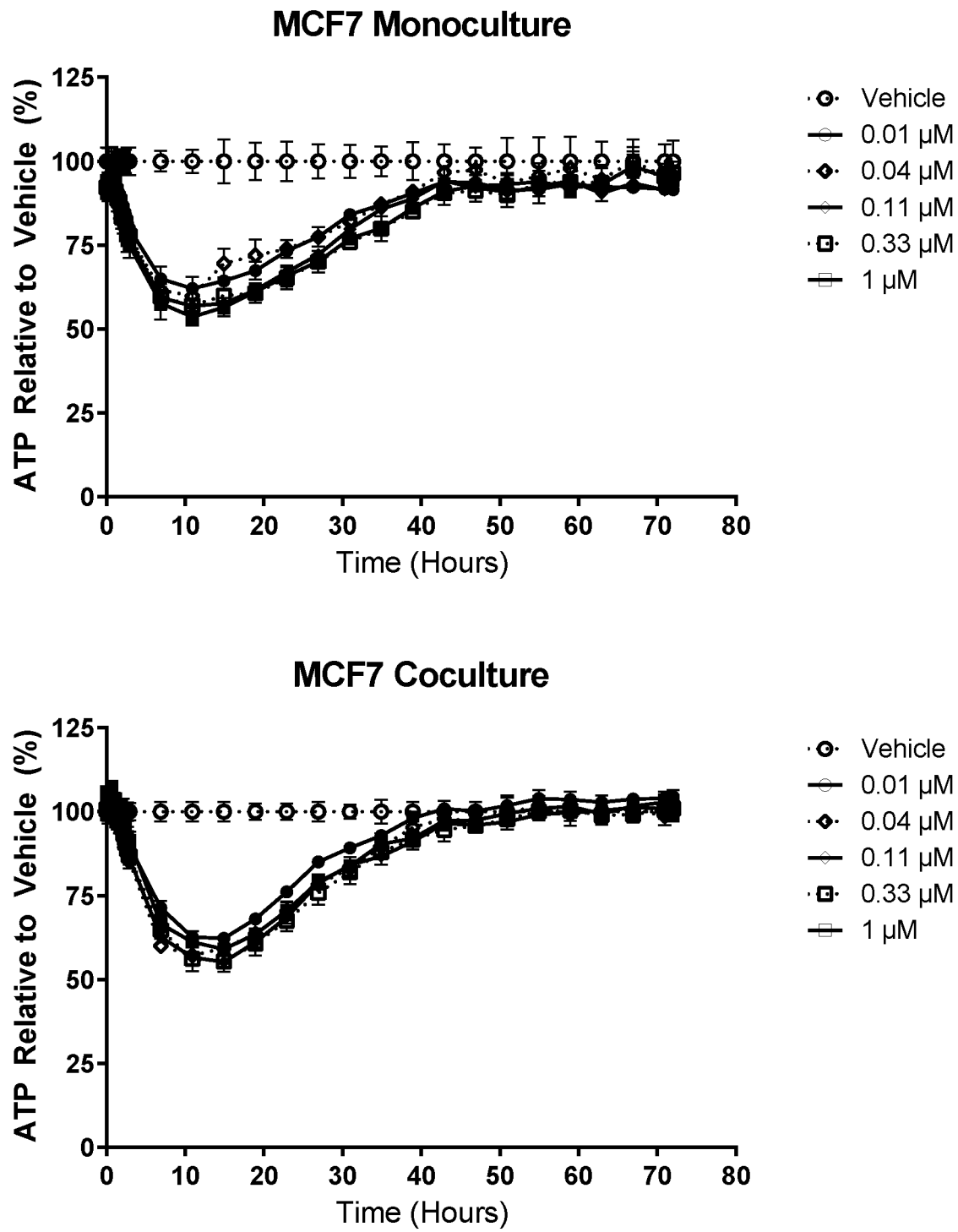

A live cell imaging approach was then utilized to evaluate the effect of cancer therapeutics on ATP levels in tumor cell lines, focusing primarily on compounds that target metabolic vulnerabilities. For example, triple-negative breast cancer (TNBC) cell lines have been shown to be more dependent on activity of GLS1, which catalyzes the first step in utilization of glutamine to fuel mitochondrial metabolism, than their receptor-positive counterparts. Using the live cell analysis approach, a rapid drop in ATP was observed upon glutamine deprivation or inhibition of GLS1 by CB-839 in TNBC cell lines. ATP levels remained below that of vehicle-treated cells for the duration of the three-day time course. In contrast, responses of receptor-positive cell lines ranged from no change to more modest decreases in ATP and full recovery within 48 hours. Quantification of phase confluence confirmed that sustained decreases in ATP were associated with enhanced antiproliferative efficacy compared to conditions under which recovery of ATP levels were observed. Further data demonstrating the ability of the ATP sensor to measure metabolic perturbations over time in tumor cells co-cultured with stromal cells was obtained. TNBC cultured on a monolayer of with CCD-1068Sk fibroblasts displayed resistance to CB-839 treatment, as measured by diminished effects on ATP levels (FIG. 5A). In contrast, results from receptor-positive breast cancer lines which showed a transient decrease in ATP levels following CB-839 treatment were unaffected by the presence of CCD-1068Sk fibroblasts (FIG. 5B).

Example 4

Lentiviral transduction was used to generate primary and iPSC-derived neurons expressing Go-ATeamA1. Expression was driven by the synapsin promoter and was restricted to neurons when lentivirus was delivered to neuronal and astrocyte co-cultures. Neurons treated with combined 2DG and KCN responded with a concentration-dependent depletion in ATP as indicated by a drop in FRET ratio. Responses were comparable to those observed following combined 2DG and KCN treatment in other mammalian cells (e.g. cancer cell lines, FIG. 4A).

SEQUENCES

SEQ ID NO: 5 - ATP Binding Protein
MKTVKVNITTPDGPVYDADIEMVSVRAESGDLGILPGHIPTKAPLKIGAVRLKKDGQ
TEMVAVSGGTVEVRPDHVTINAQAAETAEGIDKERAEAARQRAQERLNSQSDDTDI
RRAELALQRALNRLDVAGK SEO ID NO: 14 - DNA sequence encoding the ATP Binding Protein of SEQ ID NO: 1
ATGAAAACTGTGAAAGTGAATATAACAACCCCTGATGGGCCAGTCTACGACGCT
GATATCGAGATGGTGTCCGTGCGGGCCGAGAGTGGTGATCTCGGCATCCTCCCCG
GTCACATTCCCACAAAGGCCCCACTGAAGATCGGAGCTGTGCGGCTGAAGAAGG
ACGGCCAAACCGAGATGGTCGCAGTCTCAGGCGGCACTGTTGAAGTGCGGCCTG
ACCACGTTACCATTAATGCTCAAGCCGCTGAAACAGCCGAAGGAATCGACAAAG
AGAGAGCAGAAGCCGCAAGACAGAGGGCCCAGGAGCGGCTGAACTCTCAATCC
GATGACACCGATATTCGCCGGGCCGAGCTGGCACTGCAGAGGGCCCTGAACAGA
CTGGACGTGGCTGGGAAG SEQ ID NO: 15 - Control Mutant ATP Binding Protein which does not bind ATP
MKTVKVNITTPDGPVYDADIEMVSVRAESGDLGILPGHIPTKAPLKIGAVRLKKDGQ
TEMVAVSGGTVEVRPDHVTINAQAAETAEGIDKERAEAARQRAQERLNSQSDDTDI
RRAELALQKALNKLDVAGK SEQ ID NO: 16 - DNA sequence encoding the Control Mutant ATP Binding Protein of SEQ ID NO: 3
ATGAAAACTGTGAAAGTGAATATAACAACCCCTGATGGGCCAGTCTACGACGCT
GATATCGAGATGGTGTCCGTGCGGGCCGAGAGTGGTGATCTCGGCATCCTCCCCG

```
GTCACATTCCCACAAAGGCCCCACTGAAGATCGGAGCTGTGCGGCTGAAGAAGG
ACGGCCAAACCGAGATGGTCGCAGTCTCAGGCGGCACTGTTGAAGTGCGGCCTG
ACCACGTTACCATTAATGCTCAAGCCGCTGAAACAGCCGAAGGAATCGACAAAG
AGAGAGCAGAAGCCGCAAGACAGAGGGCCCAGGAGCGGCTGAACTCTCAATCC
GATGACACCGATATTCGCCGGGCCGAGCTGGCACTGCAGAAGGCCCTGAACAAG
CTGGACGTGGCTGGGAAG

SEQ ID NO: 17 - DNA sequence encoding mKOk fluorescent protein (nucleotides 1-654), a
first alanine linker (nucleotides 655-657), an ATP binding protein (nucleotides 658-1053), a
second alanine linker (nucleotides 1054-1056), and cpmEGFP fluorescent protein
(nucleotides 1057-1794)
ATGGTGAGTGTGATTAAACCAGAGATGAAGATGAGGTACTACATGGACGGCTCC
GTCAATGGGCATGAGTTCACAATTGAAGGTGAAGGCACAGGCAGACCTTACGAG
GGACATCAAGAGATGACACTACGCGTCACAATGGCCGAGGGCGGGCCAATGCCT
TTCGCGTTTGACTTAGTGTCACACGTGTTCTGTTACGGCCACAGAGTATTTACTAA
ATATCCAGAAGAGATACCAGACTATTTCAAACAAGCATTTCCTGAAGGCCTGTCA
TGGGAAAGGTCGTTGGAGTTCGAAGATGGTGGGTCCGCTTCAGTCAGTGCGCAT
ATAAGCCTTAGAGGAAACACCTTCTACCACAAATCCAAATTTACTGGGGTTAACT
TTCCTGCCGATGGTCCTATCATGCAAAACCAAAGTGTTGATTGGGAGCCATCAAC
CGAGAAAATTACTGCCAGCGACGGAGTTCTCAAGGGTGATGTTACGATGTACCT
AAAACTTGAAGGAGGCGGCAATCACAAATGCCAATTCAAGACTACTTACAAGGC
GGCAAAAGAGATTCTTGAAATGCCAGGAGACCATTACATCGGCCATCGCCTCGT
CAGGAAAACCGAAGGCAACATTACTGAGCAGGTAGAAGATGCAGTAGCTCATTC
CGCTATGAAAACTGTGAAAGTCAATATAACAACCCCTGATGGGCCAGTCTACGA
CGCTGATATCGAGATGGTGTCCGTGCGGGCCGAGAGTGGTGATCTCGGCATCCTC
CCCGGTCACATTCCCACAAAGGCCCCACTGAAGATCGGAGCTGTGCGGCTGAAG
AAGGACGGCCAAACCGAGATGGTCGCAGTCTCAGGCGGCACTGTTGAAGTGCGG
CCTGACCACGTTACCATTAATGCTCAAGCCGCTGAAACAGCCGAAGGAATCGAC
AAAGAGAGAGCAGAAGCCGCAAGACAGAGGGCCCAGGAGCGGCTGAACTCTCA
ATCCGATGACACCGATATTCGCCGGGCCGAGCTGGCACTGCAGAGGGCCCTGAA
CAGACTGGACGTGGCTGGGAAGGCTGACGGCAGCGTGCAGCTCGCCGACCACTA
CCAGCAGAACACCCCCATCGGCGACGGCCCCGTGCTGCTGCCCGACAACCACTA
CCTGAGCACCCAGTCCAAGCTGAGCAAAGACCCCAACGAGAAGCGCGATCACAT
GGTCCTGCTGGAGTTCGTGACCGCCGCCGGGATCACTCTCGGCATGGACGAGCTG
TACAAGGGTGGCAGCGGTGGCATGGTGAGCAAGGGCGAGGAGCTGTTCACCGGG
GTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGA
CCTACGGCGTGCAGTGCTTCAGCCGCTACCCCGACCACATGAAGCAGCACGACTT
CTTCAAGTCCGCCATGCCCGAAGGCTACGTCCAGGAGCGCACCATCTTCTTCAAG
GACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTG
GGGCACAAGCTGGAGTACAACTACAACAGCCACAACGTCTATATCATGGCCGAC
AAGCAGAAGAACGGCATCAAGGTGAACTTCAAGATCCGCCACAACATCGAGGAA
GCT SEQ ID NO: 7 - Fusion Protein encoded by SEQ ID NO: 17 - including mKOk fluorescent
protein (amino acids 1-218), a first alanine linker (amino acid 219), an ATP binding protein
(amino acids 220-351), a second alanine linker (amino acid 352), and cpmEGFP fluorescent
protein (amino acids 352-598)
MVSVIKPEMKMRYYMDGSVNGHEFTIEGEGTGRPYEGHQEMTLRVTMAEGGPMPF
AFDLVSHVFCYGHRVFTKYPEEIPDYFKQAFPEGLSWERSLEFEDGGSASVSAHISLR
GNTFYHKSKFTGVNFPADGPIMQNQSVDWEPSTEKITASDGVLKGDVTMYLKLEGG
GNHKCQFKTTYKAAKEILEMPGDRYIGHRLVRKTEGNITEQVEDAVAHSAMKTVKV
NITTPDGPVYDADIEMVSVRAESGDLGILPGHIPTKAPLKIGAVRLKKDGQTEMVAVS
GGTVEVRPDHVTINAQAAETAEGIDKERAEAARQRAQERLNSQSDDTDIRRAELALQ
RALNRLDVAGKADGSVQLADHYQQNTPIGDGPVLLPDNHYLSTQSKLSKDPNEKRD
HMVLLEFVTAAGITLGMDELYKGGSGGMVSKGEELFTGVVPILVELDGDVNGHKFS
VSGEGEGDATYGKLTLKFICTTGKLPVPWPTLVTTLTYGVQCFSRYPDHMKQHDFF
KSAMPEGYVQERTIFFKDDGNYKTRAEVKFEGDTLVNRIELKGIDFKEDGNILGHKL
EYNYNSHNVYIMADKQKNGIKVNFKIRHNIEEA GO-ATeam-A1 control
SEQ ID NO: 18 - DNA encoding mKOk fluorescent protein (nucleotides 1-654), a first
alanine linker (nucleotides 655-657), a control ATP Binding protein mutated so it not bind
ATP (nucleotides 658-1053), a second alanine linker (nucleotides 1054-1056), and
cpmEGFP fluorescent protein (nucleotides 1057-1794)
ATGGTGAGTGTGATTAAACCAGAGATGAAGATGAGGTACTACATGGACGGCTCC
GTCAATGGGCATGAGTTCACAATTGAAGGTGAAGGCACAGGCAGACCTTACGAG
GGACATCAAGAGATGACACTACGCGTCACAATGGCCGAGGGCGGGCCAATGCCT
TTCGCGTTTGACTTAGTGTCACACGTGTTCTGTTACGGCCACAGAGTATTTACTAA
ATATCCAGAAGAGATACCAGACTATTTCAAACAAGCATTTCCTGAAGGCCTGTCA
TGGGAAAGGTCGTTGGAGTTCGAAGATGGTGGGTCCGCTTCAGTCAGTGCGCAT
ATAAGCCTTAGAGGAAACACCTTCTACCACAAATCCAAATTTACTGGGGTTAACT
TTCCTGCCGATGGTCCTATCATGCAAAACCAAAGTGTTGATTGGGAGCCATCAAC
CGAGAAAATTACTGCCAGCGACGGAGTTCTCAAGGGTGATGTTACGATGTACCT
AAAACTTGAAGGAGGCGGCAATCACAAATGCCAATTCAAGACTACTTACAAGGC
```

```
                              SEQUENCES
GGCAAAAGAGATTCTTGAAATGCCAGGAGACCATTACATCGGCCATCGCCTCGT
CAGGAAAACCGAAGGCAACATTACTGAGCAGGTAGAAGATGCAGTAGCTCATTC
CGCTATGAAAACTGTGAAAGTGAATATAACAACCCCTGATGGGCCAGTCTACGA
CGCTGATATCGAGATGGTGTCCGTGCGGGCCGAGAGTGGTGATCTCGGCATCCTC
CCCGGTCACATTCCCACAAAGGCCCCACTGAAGATCGGAGCTGTGCGGCTGAAG
AAGGACGGCCAAACCGAGATGGTCGCAGTCTCAGGCGGCACTGTTGAAGTGCGG
CCTGACCACGTTACCATTAATGCTCAAGCCGCTGAAACAGCCGAAGGAATCGAC
AAAGAGAGAGCAGAAGCCGCAAGACAGAGGGCCCAGGAGCGGCTGAACTCTCA
ATCCGATGACACCGATATTCGCCGGGCCGAGCTGGCACTGCAGAAGGCCCTGAA
CAAGCTGGACGTGGCTGGGAAGGCTGACGGCAGCGTGCAGCTCGCCGACCACTA
CCAGCAGAACACCCCCATCGGCGACGCCCCGTGCTGCTGCCCGACAACCACTA
CCTGAGCACCCAGTCCAAGCTGAGCAAAGACCCCAACGAGAAGCGCGATCACAT
GGTCCTGCTGGAGTTCGTGACCGCCGCCGGGATCACTCTCGGCATGGACGAGCTG
TACAAGGGTGGCAGCGGTGGCATGGTGAGCAAGGGCGAGGAGCTGTTCACCGGG
GTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGA
CCTACGGCGTGCAGTGCTTCAGCCGCTACCCCGACCACATGAAGCAGCACGACTT
CTTCAAGTCCGCCATGCCCGAAGGCTACGTCCAGGAGCGCACCATCTTCTTCAAG
GACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTG
GGGCACAAGCTGGAGTACAACTACAACAGCCACAACGTCTATATCATGGCCGAC
AAGCAGAAGAACGGCATCAAGGTGAACTTCAAGATCCGCCACAACATCGAGGAA
GCT

SEQ ID NO: 19 - Fusion Protein encoded by SEQ ID NO: 18 - including mKOk fluorescent
protein (amino acids 1-218), a first alanine linker (amino acid 219), a control mutant ATP
binding protein which does not bind ATP (amino acids 220-351), a second alanine linker
(amino acid 352), and cpmEGFP fluorescent protein (amino acids 352-598)
MVSVIKPEMKMRYYMDGSVNGHEFTIEGEGTGRPYEGHQEMTLRVTMAEGGPMPF
AFDLVSHVFCYGHRVFTKYPEEIPDYFKQAFPEGLSWERSLEFEDGGSASVSAHISLR
GNTFYHKSKFTGVNFPADGPIMQNQSVDWEPSTEKITASDGVLKGDVTMYLKLEGG
GNHKCQFKTTYKAAKEILEMPGDHYIGHRLVRKTEGNITEQVEDAVAHSAMKTVKV
NITTPDGPVYDADIEMVSVRAESGDLGILPGHIPTKAPLKIGAVRLKKDGQTEMVAVS
GGTVEVRPDHVTINAQAAETAEGIDKERAEAARQRAQERLNSQSDDTDIRRAELALQ
KALNKLDVAGKADGSVQLADHYQQNTPIGDGPVLLPDNHYLSTQSKLSKDPNEKRD
HMVLLEFVTAAGITLGMDELYKGGSGGMVSKGEELFTGVVPILVELDGDVNGHKFS
VSGEGEGDATYGKLTLKFICTTGKLPVPWPTLVTTLTYGVQCFSRYPDHMKQHDFF
KSAMPEGYVQERTIFFKDDGNYKTRAEVKFEGDTLVNRIELKGIDFKEDGNILGHKL
EYNYNSHNVYIMADKQKNGIKVNFKIRHNIEEA
```

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the disclosure. Changes therein and other uses will occur to those skilled in the art. Such changes and other uses can be made without departing from the scope of the disclosure as set forth in the claims.

We claim:

1. A polynucleotide comprising a nucleic acid encoding a fusion protein of genus X1-X2-X3-X4-X5, wherein:
   X1 is a FRET acceptor polypeptide consisting of the amino acid sequence of SEQ ID NO: 1, and X5 is a FRET donor polypeptide consisting of the amino acid sequence of SEQ ID NO: 4;
   X2 and X4 are selected from the group consisting of (i) X2 is A and X4 is A; (ii) X2 is S and X4 is SA; (iii) X2 is S and X4 is A; (iv) X2 is absent and X4 is GA; (v) X2 is absent and X4 is FF; and (vi) X2 is T and X4 is GTSG; and
   X3 is an ATP binding protein consisting of the amino acid sequence of SEQ ID NO: 5;
   wherein binding of ATP by the ATP binding protein causes interaction of the FRET acceptor polypeptide and the FRET donor polypeptide.

2. An expression vector comprising the polynucleotide of claim 1, wherein the polynucleotide is operatively linked to a promoter sequence capable of directing expression of the fusion protein.

3. A recombinant host cell comprising the expression vector of claim 2.

4. A kit comprising:
   (a) the polynucleotide of claim 1; and
   (b) a control polynucleotide, wherein the control polynucleotide comprises a nucleic acid encoding a control fusion protein of genus X1-X2-X3-X4-X5, wherein:
   X1 is a polypeptide consisting of the amino acid sequence of SEQ ID NO: 1, and X5 is a polypeptide consisting of the amino acid sequence of SEQ ID NO: 4;
   X2 and X4 are selected from the group consisting of (i) X2 is A and X4 is A; (ii) X2 is S and X4 is SA; (iii) X2 is S and X4 is A; (iv) X2 is absent and X4 is GA; (v) X2 is absent and X4 is FF; and (vi) X2 is T and X4 is GTSG; and
   X3 is a polypeptide consisting of the amino acid sequence of SEQ ID NO: 12.

5. A method of assaying ATP, comprising:
   (a) expressing the fusion protein encoded by the polynucleotide of claim 1 in one or more first cells, and generating one or more images selected from the group consisting of:
      (i) a fluorescence image generated by detecting fluorescent signals produced by light having the FRET acceptor polypeptide emission wavelength emitted from the one or more first cells upon exposing the one or more first cells to light having the FRET donor polypeptide excitation wavelength;
      (ii) a fluorescence image generated by detecting fluorescent signals produced by light having the FRET acceptor polypeptide emission wavelength emitted from the one or more first cells upon exposing the one or more first cells to light having the FRET acceptor polypeptide excitation wavelength;
      (iii) a fluorescence image generated by detecting fluorescent signals produced by light having the FRET donor polypeptide emission wavelength emitted from the one or more first cells upon exposing the one or more first cells to light having the FRET donor polypeptide excitation wavelength; and
      (iv) any combinations of (i), (ii), and (iii); and
   (b) determining a FRET ratio in the one or more first cells by comparing the output of fluorescent signals in the fluorescent image of (i), the fluorescent image of (ii), and/or the fluorescent image of (iii); wherein the level of ATP in the one or more first cells is proportional to the determined FRET ratio.

6. The polynucleotide of claim 1, wherein X2 is A and X4 is A.

7. The polynucleotide of claim 1, wherein the fusion protein comprises the amino acid sequence selected from the group consisting of SEQ ID NO: 7, 8, 9, 10, and 11.

8. The kit of claim 4, wherein the control polynucleotide encodes a control fusion protein comprising the amino acid sequence of SEQ ID NO: 13.

9. The polynucleotide of claim 1, wherein the fusion protein comprises the amino acid sequence of SEQ ID NO: 7.

10. An expression vector comprising the polynucleotide of claim 6, wherein the polynucleotide is operatively linked to a promoter sequence capable of directing expression of the fusion protein.

11. An expression vector comprising the polynucleotide of claim 7, wherein the polynucleotide is operatively linked to a promoter sequence capable of directing expression of the fusion protein.

12. An expression vector comprising the polynucleotide of claim 9, wherein the polynucleotide is operatively linked to a promoter sequence capable of directing expression of the fusion protein.

13. A recombinant host cell comprising the expression vector of claim 10.

14. A recombinant host cell comprising the expression vector of claim 11.

15. A recombinant host cell comprising the expression vector of claim 12.

16. The kit of claim 4, wherein the polynucleotide encodes a fusion protein, wherein the fusion protein comprises the amino acid sequence selected from the group consisting of SEQ ID NO: 7, 8, 9, 10, and 11.

17. The kit of claim 4, wherein the polynucleotide encodes a fusion protein, wherein the fusion protein comprises the amino acid sequence of SEQ ID NO: 7.

18. The kit of claim 17, wherein the control polynucleotide encodes a control fusion protein comprising the amino acid sequence of SEQ ID NO: 13.

19. The kit of claim 4, wherein (i) the polynucleotide is present in a first expression vector, wherein the polynucleotide is operatively linked to a promoter sequence capable of directing expression of the fusion protein; and (ii) the control polynucleotide is present in a second expression vector, wherein the control polynucleotide is operatively linked to a promoter sequence capable of directing expression of the control fusion protein.

20. The kit of claim 16, wherein (i) the polynucleotide is present in a first expression vector, wherein the polynucleotide is operatively linked to a promoter sequence capable of directing expression of the fusion protein; and (ii) the control polynucleotide is present in a second expression vector, wherein the control polynucleotide is operatively linked to a promoter sequence capable of directing expression of the control fusion protein.

21. The kit of claim 17, wherein (i) the polynucleotide is present in a first expression vector, wherein the polynucleotide is operatively linked to a promoter sequence capable of directing expression of the fusion protein; and (ii) the control polynucleotide is present in a second expression vector, wherein the control polynucleotide is operatively linked to a promoter sequence capable of directing expression of the control fusion protein.

22. The kit of claim 18, wherein (i) the polynucleotide is present in a first expression vector, wherein the polynucleotide is operatively linked to a promoter sequence capable of directing expression of the fusion protein; and (ii) the control polynucleotide is present in a second expression vector, wherein the control polynucleotide is operatively linked to a promoter sequence capable of directing expression of the control fusion protein.

* * * * *

UNITED STATES PATENT AND TRADEMARK OFFICE
CERTIFICATE OF CORRECTION

PATENT NO. : 12,158,470 B2
APPLICATION NO. : 16/765908
DATED : December 3, 2024
INVENTOR(S) : Appledorn et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 970 days.

Signed and Sealed this
Eighteenth Day of March, 2025

Coke Morgan Stewart
*Acting Director of the United States Patent and Trademark Office*